(12) United States Patent
Blaesi et al.

(10) Patent No.: US 11,285,116 B2
(45) Date of Patent: Mar. 29, 2022

(54) METHOD FOR THE MANUFACTURE OF FIBROUS DOSAGE FORMS

(71) Applicant: Aron H. Blaesi, Cambridge, MA (US)

(72) Inventors: Aron H. Blaesi, Cambridge, MA (US); Nannaji Saka, Cambridge, MA (US)

(73) Assignee: Aron H. Blaesi, Cambridge, MA (US)

( * ) Notice: Subject to any disclaimer, the term of this patent is extended or adjusted under 35 U.S.C. 154(b) by 0 days.

(21) Appl. No.: 16/861,202

(22) Filed: Apr. 28, 2020

(65) Prior Publication Data

US 2021/0169821 A1 Jun. 10, 2021

Related U.S. Application Data

(63) Continuation of application No. 15/964,058, filed on Apr. 26, 2018, now Pat. No. 10,751,292, which is a continuation-in-part of application No. PCT/US2017/047703, filed on Aug. 19, 2017.

(60) Provisional application No. 62/468,888, filed on Mar. 8, 2017, provisional application No. 62/446,431, filed
(Continued)

(51) Int. Cl.
| | |
|---|---|
| *A61K 9/70* | (2006.01) |
| *A61K 47/10* | (2017.01) |
| *A61K 31/192* | (2006.01) |
| *A61K 47/34* | (2017.01) |
| *D04H 3/05* | (2006.01) |
| *D04H 3/007* | (2012.01) |
| *A61K 31/167* | (2006.01) |
| *B29C 48/05* | (2019.01) |
| *B29C 48/00* | (2019.01) |
| *B29C 48/395* | (2019.01) |
| *B29K 29/00* | (2006.01) |
| *B29K 105/00* | (2006.01) |
| *B29L 31/00* | (2006.01) |

(52) U.S. Cl.
CPC .............. *A61K 9/70* (2013.01); *A61K 31/167* (2013.01); *A61K 31/192* (2013.01); *A61K 47/10* (2013.01); *A61K 47/34* (2013.01); *B29C 48/022* (2019.02); *B29C 48/05* (2019.02); *B29C 48/397* (2019.02); *D04H 3/007* (2013.01); *D04H 3/05* (2013.01); *B29K 2029/04* (2013.01); *B29K 2105/0035* (2013.01); *B29L 2031/753* (2013.01); *D10B 2321/06* (2013.01); *D10B 2331/06* (2013.01); *D10B 2509/00* (2013.01)

(58) Field of Classification Search
CPC ..... B29C 64/10; B29C 64/106; B29C 64/112; B29C 64/118; B29C 64/124; B29C 64/165; B29C 64/20; B29C 64/205; B29C 64/227; B29C 64/241; B29C 64/245; B29C 64/40
See application file for complete search history.

(56) References Cited

U.S. PATENT DOCUMENTS

| | | | |
|---|---|---|---|
| 2006/0094744 A1* | 5/2006 | Maryanoff ........... | A61K 31/445 514/291 |
| 2013/0261188 A1* | 10/2013 | Hibi .................... | A61K 31/192 514/570 |
| 2019/0125681 A1* | 5/2019 | Albed Alhnan ...... | B29C 64/209 |

* cited by examiner

*Primary Examiner* — Nahida Sultana

(57) ABSTRACT

Recently, we have introduced fibrous dosage forms that enable predictable microstructures with a greater range of pharmaceutically relevant properties. Presented herein, accordingly, is a method for the manufacture of such fibrous dosage forms. The method includes extruding a plasticized matrix through an exit port of an extrusion channel to form one or more plasticized fibers, structuring said fibers to a three dimensional structural network by patterning on a translating or rotating stage, and solidifying the patterned structure.

24 Claims, 25 Drawing Sheets

Related U.S. Application Data on Jan. 14, 2017, provisional application No. 62/377,068, filed on Aug. 19, 2016.

METHOD FOR THE MANUFACTURE OF FIBROUS DOSAGE FORMS

CROSS-REFERENCE TO RELATED APPLICATIONS

This application is a continuation of, and incorporates herein by reference in its entirety, the U.S. application Ser. No. 15/964,058 and titled "Method and apparatus for the manufacture of fibrous dosage forms", which is a continuation-in-part of the International Application No. PCT/US17/47703 filed on Aug. 19, 2017 and titled "Method and apparatus for the manufacture of fibrous dosage forms", which claims priority to and the benefit of the U.S. provisional application Nos. U.S. 62/377,068 filed on Aug. 19, 2016, U.S. 62/446,431 filed on Jan. 14, 2017, and U.S. 62/468,888 filed on Mar. 8, 2017. All foregoing applications are hereby incorporated by reference in their entirety.

This application is related to, and incorporates herein by reference in its entirety, the U.S. application Ser. No. 14/907,891 filed on Jan. 27, 2016 and titled "Melt-Processed Polymeric Cellular Dosage Form". This application is also related to, and incorporates herein by reference in its entirety, the U.S. application Ser. No. 15/482,776 filed on Apr. 9, 2017 and titled "Fibrous dosage form". Further, this application is related to, and incorporates herein by reference in its entirety, the U.S. application Ser. No. 16/246,456 filed on Jan. 11, 2019 and titled "Method and apparatus for the manufacture of cellular solids".

FIELD OF THE INVENTION

This invention relates generally to methods for the manufacture of fibrous solids, and more particularly to methods for the manufacture of fibrous dosage forms with predictable microstructure. The apparatus to produce the product and the product obtained by the method herein are also included in this invention.

BACKGROUND OF THE INVENTION

The most prevalent pharmaceutical dosage forms at present, the porous, oral-delivery tablets, are manufactured by mixing and compacting drug and excipient powders. Although powder processing is extensively used in the manufacture of oral dosage forms, it has inherent limitations: mixing is fraught with particle segregation and agglomeration, and compacting with non-deterministic porosity. As a result, the dosage form microstructure, drug content, and drug release rate are difficult to control tightly, and their range is limited. Moreover, dosage form manufacture is by a resource-intensive and time-consuming batch process. Further details about the design and manufacture of state-of-the-art dosage forms are given in the commonly owned references "Remington's Pharmaceutical Sciences XVIII", A. R. Gennaro (ed.), Mack Publishing, Easton, Pa., 1990; M. E. Aulton, K. M. G. Taylor, "Aulton's pharmaceutics: The design and manufacture of medicines", fourth edition, Churchill Livingstone, London, UK, 2013; F. J. Muzzio, T. Shinbrot, B. J. Glasser, "Powder technology in the pharmaceutical industry: the need to catch up fast", Powder Technol. 124 (2002) 1-7; T. A. Bell, "Challenges in the scale-up of particulate processes—an industrial perspective", Powder Technol. 150 (2005) 60-71; and "Pharmaceutical Manufacturing Handbook: Regulations and Quality", S. Cox Gad (Ed.), John Wiley & Sons, Inc., Hoboken, N.J., 2008.

The difficulties associated with processing powders could be circumvented, however, by transitioning to the predictable liquid-based processing. Therefore, in the commonly owned U.S. patent application Ser. No. 14/907,891, the U.S. patent application Ser. No. 15/482,776, and the publications in J. Control. Release, 220 (2015) 397-405; Eur. J. Pharm. Biopharm, 103 (2016) 210-218; Int. J. Pharm. 509 (2016) 444-453; Chem. Eng. J. 320 (2017) 549-560; Mater. Sci. Eng. C 80 (2017) 715-727; and Mater. Sci. Eng. C 84 (2018) 218-229, the present inventors (Blaesi and Saka) have introduced cellular and fibrous dosage forms. These dosage forms comprise solid frameworks of a drug-excipient composite (or a solid solution) and gas-filled cells or voids. It was shown that both the microstructure and the drug release rate are predictable and precisely controllable; the release rate was predominantly determined by the physico-chemical properties of the excipient, the connectivity of the void space, the cell size (or inter-fiber spacing in the case of fibrous dosage forms), and the wall thickness (or fiber radius).

In this disclosure, a method for the manufacture of fibrous structures is presented. The disclosed method enables fast and economical manufacture of dosage forms with precisely controlled microstructure and properties. It further enables the manufacture of dosage forms with a greater range of properties (e.g., a greater range of the drug release rate, drug content, etc.), and the continuous manufacture of personalized dosage forms, among others.

SUMMARY OF THE INVENTION

In one aspect of the continuous (or semi-continuous or batch) process to manufacture pharmaceutical solid dosage forms disclosed herein, one or more solid constituents are first injected into an extrusion channel having a cross section extending along its length inside a housing. Also, at least one solvent is injected into said extrusion channel to solvate at least one injected solid constituent so that the one or more injected solid constituents form a plasticized matrix. The plasticized matrix is conveyed towards an exit port of the extrusion channel by applying mechanical work on the plasticized matrix. Then the plasticized matrix is extruded through an exit port to form at least one plasticized fiber. Subsequently, said at least one plasticized fiber is structured to a three dimensional structural network of one or more drug-containing fibers.

In another aspect, one or more solid constituents are first injected into an extrusion channel having a cross section extending along its length inside a housing. The injected one or more solid constituents are then heated to form a plasticized matrix. The plasticized matrix is conveyed towards an exit port of the extrusion channel by applying mechanical work on the plasticized matrix. Then the plasticized matrix is extruded through an exit port to form at least one plasticized fiber. Subsequently, said at least one plasticized fiber is structured to a three dimensional structural network of one or more drug-containing fibers.

In a further aspect, at least one plasticized matrix is first injected into an extrusion channel having a cross section extending along its length inside a housing. The at least one plasticized matrix is then conveyed towards an exit port of the extrusion channel by applying mechanical work on the at least one plasticized matrix. The at least one plasticized matrix is then extruded through an exit port to form at least one plasticized fiber. Subsequently, said at least one plasticized fiber is structured a three dimensional structural network of one or more drug-containing fibers.

In certain embodiments, one or more plasticized fibers are structured to a three dimensional structural network by depositing said fibers along a path defined by motion of a translating or rotating stage.

In certain embodiments, the stage is movable in at least three directions relative to an exit port for depositing one or more plasticized fibers along a path defined by motion of said stage.

In certain embodiments, two directions in which the stage is movable span a plane oriented at an angle to the central axis of the extruded fiber to pattern said fiber on a substrate defined by or attached to said stage, and wherein said stage is further movable in a third direction oriented at an angle to said plane to control the distance between said substrate and an exit port.

In certain embodiments of the aspects above, the three dimensional structural network of one or more drug-containing fibers is further solidified.

In certain embodiments, the three dimensional structural network of one or more drug-containing fibers is solidified by evaporating solvent from at least one plasticized fiber.

In certain embodiments, the three dimensional structural network of one or more drug-containing fibers is solidified by cooling at least one plasticized fiber to below its melting temperature.

In certain embodiments, the deposited three dimensional structural network of one or more fibers is solidified by application of a gas flow through said network.

In certain embodiments, gas is blown on a plasticized fiber to increase the rate at which said fiber solidifies.

In certain embodiments, the far-field velocity of said gas is greater than 0.1 m/s.

In certain embodiments, gas flow is applied using a gas blowing unit.

In certain embodiments, gas flow through the deposited fiber network promotes solidification by evaporating solvent or by cooling.

In certain embodiments, the stage comprises at least a perforation through which gas flows for solidifying the deposited structure.

In certain embodiments, the stage comprises a solid grid having at least a perforation through which gas flows for solidifying the deposited structure.

In certain embodiments, at least one exit port is designed to extrude fiber having a fiber thickness less than 2.5 mm.

In certain embodiments, the application of mechanical work on the plasticized matrix is performed using a conveying element.

In certain embodiments, at least one conveying element is a screw.

In certain embodiments, the conveying element is selected from the group comprising screws, pistons, or fluid pumps.

In certain embodiments, the structuring of at least one plasticized fiber to a three dimensional network of one or more drug-containing fibers is performed using a translating or rotating stage.

In certain embodiments, the structuring of at least one plasticized fiber to a three dimensional structural network of one or more drug-containing fibers is performed by 3D-patterning said at least one plasticized fiber on a substrate.

In certain embodiments, a substrate is defined by or attached to a translating or rotating stage.

In certain embodiments, the velocity of a substrate with respect to an exit port is in the range 0.1-10 times the velocity of a plasticized fiber with respect to said exit port.

In certain embodiments, the distance between an exit port and the deposition location of a fibrous extrudate is no greater than 7 mm.

In certain embodiments, the thickness of a fiber in the fibrous dosage form is precisely controlled.

In certain embodiments, an inter-fiber spacing in the fibrous dosage form is precisely controlled.

In certain embodiments, the position of an inter-fiber contact and the contact width of said inter-fiber contact in the fibrous dosage form are precisely controlled.

In certain embodiments, the shear viscosity of a fibrous extrudate is greater than 0.01 Pa·s.

In certain embodiments, the weight fraction of solvent in a plasticized fiber is no greater than 0.925.

Furthermore, in certain embodiments of the aspects above, the extrusion channel cross section tapers down before an exit port to the cross section of said exit port.

In certain embodiments, the extrusion channel bifurcates into at least one other end comprising an exit port.

In certain embodiments, the injection of one or more solid constituents through the first feeding port into the extrusion channel is performed using a solids feeding unit.

In certain embodiments, at least one solid constituent is injected as a granular solid.

In certain embodiments, the injection of at least one solvent into the extrusion channel is performed using a solvent feeding unit attached to at least a second feeding port.

In certain embodiments, at least one injected constituent comprises an active pharmaceutical ingredient.

In certain embodiments, the housing comprises at least one sensing port for attaching a sensor to the extrusion channel.

In certain embodiments, at least one sensor is attached to a sensing port.

In certain embodiments, said at least one sensor is selected from the group comprising pressure sensors, temperature sensors, flow rate sensors, composition sensors, or sensors for measuring the physical form of the material in the extrusion channel.

In certain embodiments, the pharmaceutical solid dosage forms comprise a drug-containing solid having an outer surface and an internal structure contiguous with and terminating at said outer surface, said internal structure comprising a three dimensional structural network of one or more drug-containing fibers, said fibers further comprising fiber segments separated and spaced from adjoining fiber segments by free spacings defining one or more free spaces in the drug-containing solid.

In certain embodiments, the one or more fibers in the three dimensional structural network of fibers comprise an average thickness no greater than 2.5 mm.

In certain embodiments, the effective free spacing between the fiber segments across the one or more free spaces of the drug-containing solid on average is greater than 0.1 μm.

In certain embodiments, a contact width between two fibers or two fiber segments in the three dimensional structural network of fibers is no greater than 2.5 mm.

In another aspect, the invention herein comprises a pharmaceutical solid dosage form comprising a drug-containing solid comprising a three dimensional fiber network structure; said three dimensional fiber network structure comprising one or more fibers with average fiber thickness in the range of 1.75 μm to 2.5 mm; said fibers having at least one active ingredient and at least one excipient through the fiber thickness; said fibers further comprising fiber segments separated and spaced from adjoining fiber segments by free spacings; and the free spacings defining one or more free spaces in the drug-containing solid; wherein the dosage form is manufactured by a method comprising the steps of: injecting one or more active ingredients and one or more excipients into an extrusion channel having a cross section extending along its length inside a housing, wherein at least one excipient melts upon heating; heating the injected one or more active ingredients and one or more excipients to form a plasticized matrix; conveying the plasticized matrix towards an exit port of the extrusion channel by applying mechanical work on the plasticized matrix; extruding the plasticized matrix through an exit port to form at least one plasticized fiber; structuring one or more plasticized fibers to a three dimensional structural network by depositing said fibers along a path defined by motion of a translating or rotating stage; and solidifying the deposited three dimensional structural network of one or more fibers by application of a gas flow through said network.

In another aspect, the invention herein comprises a pharmaceutical solid dosage form comprising a drug-containing solid comprising a three dimensional fiber network structure; said three dimensional fiber network structure comprising one or more fibers with average fiber thickness in the range of 1.75 µm to 2.5 mm; said fibers having at least one active ingredient and at least one excipient through the fiber thickness; said fibers further comprising fiber segments separated and spaced from adjoining fiber segments by free spacings; and the free spacings defining one or more free spaces in the drug-containing solid; wherein the dosage form is manufactured by a method comprising the steps of: injecting at least one active ingredient and at least one excipient into an extrusion channel having a cross section extending along its length inside a housing; injecting at least one solvent into said extrusion channel to solvate at least one injected excipient and form a plasticized matrix; conveying the plasticized matrix towards an exit port of the extrusion channel by applying mechanical work on the plasticized matrix; extruding the plasticized matrix through an exit port to form at least one plasticized fiber; structuring one or more plasticized fibers to a three dimensional structural network by depositing said fibers along a path defined by motion of a translating or rotating stage; and solidifying the deposited three dimensional structural network of one or more fibers by application of a gas flow through said network.

Additional elements of the method and dosage form disclosed herein are described throughout this specification. Elements of embodiments described with respect to one aspect of the invention can be applied with respect to another aspect. By way of example but not by way of limitation, certain embodiments of the method claims can include features of the dosage form claims, and vice versa.

This invention may be better understood by reference to the accompanying drawings, attention being called to the fact that the drawings are primarily for illustration, and should not be regarded as limiting.

BRIEF DESCRIPTION OF THE DRAWINGS

The objects, embodiments, features, and advantages of the present invention are more fully understood when considered in conjunction with the following accompanying drawings.

DEFINITIONS

Figure 1:
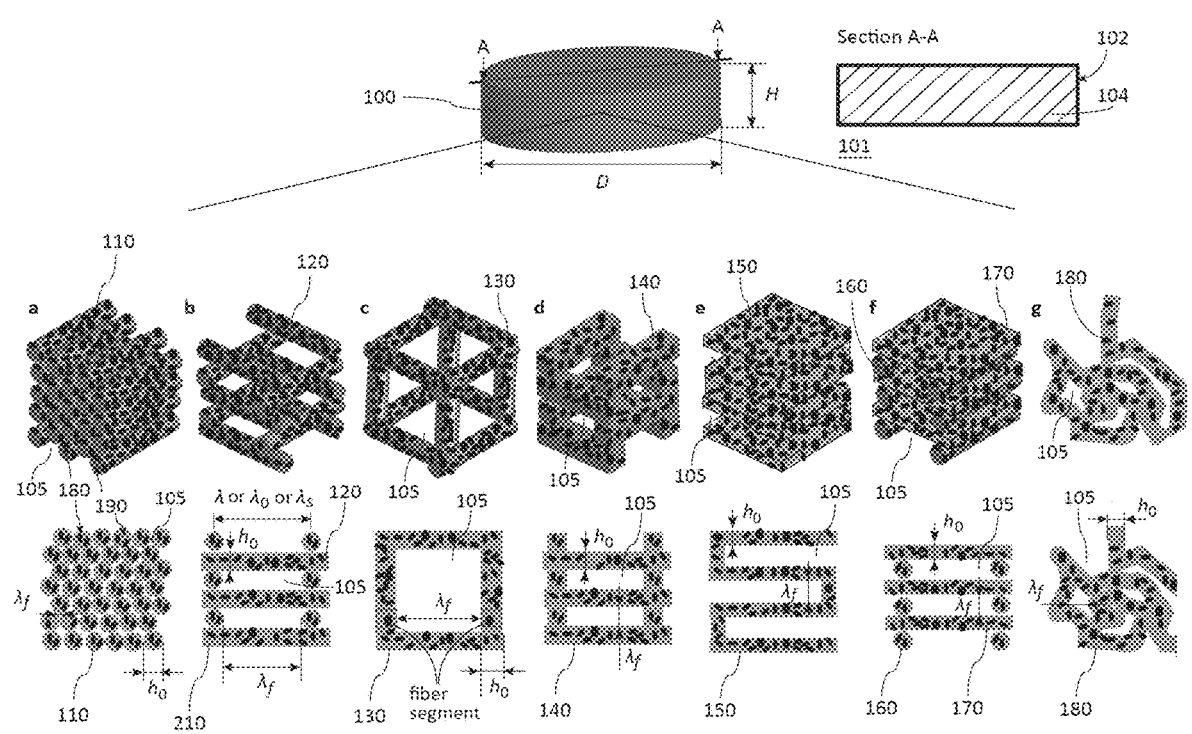
FIG. 1 presents schematic diagrams of the microstructural topology of fibrous dosage forms according to this invention.

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises" are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art.

Moreover, in the disclosure herein, the terms "one or more active ingredients", "active ingredient", "active pharmaceutical ingredient", and "drug" are used interchangeably. As used herein, an "active ingredient" or "active agent" refers to an agent whose presence or level correlates with elevated level or activity of a target, as compared with that observed absent the agent (or with the agent at a different level). In some embodiments, an active ingredient is one whose presence or level correlates with a target level or activity that is comparable to or greater than a particular reference level or activity (e.g., that observed under appropriate reference conditions, such as presence of a known active agent, e.g., a positive control).

A granular solid in this disclosure is a conglomeration of discrete solid particles of a specific composition. The average size of the particulates (e.g., the average diameter or the third root of the average volume) may be in the range from about 0.001 µm or smaller to about 150 mm or greater. This includes, but is not limited to an average size of the particulates of 0.002 µm-200 mm, 0.005 µm-200 mm, 0.01 µm-150 mm, 0.05 µm-150 mm, 0.1 µm-150 mm; 1 µm-100 mm, 1 µm-50 mm, 5 µm-50 mm, 10 µm-50 mm, or 5 µm-30 mm.

In the invention herein, a "solid" or "solid material" is typically referred to an elastic or visco-elastic material. Such elastic or viscoelastic materials may be characterized by a very large viscosity that may be far greater than about $10^5$ Pa·s. This includes, but is not limited to a viscosity greater than $10^7$ Pa·s, or greater than $10^{10}$ Pa·s. In the limiting case, the viscosity is so large that it is difficult to measure. A solid material may be considered "fully elastic" or "elastic" in this case. For further details about the mechanical behavior of elastic or visco-elastic materials, see, e.g., K. L. Johnson, "Contact mechanics", Cambridge University Press, 1985.

In the context of the invention herein, a plasticized matrix is a viscous material comprising a minimum shear viscosity of 0.003 Pa·s-5×$10^9$ Pa·s at a shear rate no greater than 10 l/s. This includes but is not limited to a minimum shear viscosity of 0.005 Pa·s-5×$10^9$, 0.01 Pa·s-5×$10^9$ Pa·s, 0.025 Pa·s-10,000,000 Pa·s, 0.05 Pa·s-5,000,000 Pa·s, 0.1 Pa·s-2,000,000 Pa·s, 0.25 Pa·s-1,000,000 Pa·s, 0.25 Pa·s-5,000,000 Pa·s, 0.5 Pa·s-2,000,000 Pa·s, 1 Pa·s-2,000,000 Pa·s, 1 Pa·s-5,000,000 Pa·s, 1 Pa·s-1,000,000 Pa·s, or 1 Pa·s-500,000 Pa·s at a shear rate no greater than 10 l/s. Non-limiting examples of plasticized matrices include but are not limited to polymer melts, concentrated solutions of one or more polymers and one or more solvents (e.g., water, ethanol, acetone, isopropanol, ethyl acetate, dimethyl sulfoxide, etc.), suspensions of solid particulates or granules and a polymer melt, or suspensions of solid particulates and a concentrated polymeric solution, etc. It may be noted that in the context of the invention herein the terms "plasticized matrix", "plasticized matrices", "plasticized material", and "melt" are used interchangeably. Furthermore, in some embodiments a plasticized matrix may include an active ingredient. The active ingredient may be molecularly dissolved in the plasticized matrix, dispersed as particles, etc.

Furthermore, in some embodiments of the invention herein, a three dimensional structural network of drug-containing fibers comprises a drug-containing fibrous structure (e.g., an assembly or an assemblage of one or more fibers) that extends over a length, width, and thickness greater than 200 µm. This includes, but is not limited to drug-containing fibrous structures that extend over a length, width, and thickness greater than 300 µm, or greater than 500 µm, or greater than 700 µm, or greater than 1 mm, or greater than 1.25 mm, or greater than 1.5 mm, or greater than 2 mm.

In other embodiments, a three dimensional structural network of drug-containing fibers may comprise a drug-containing fibrous structure (e.g., an assembly or an assemblage of one or more fibers) that extends over a length, width, and thickness greater than the average thickness of at least one fiber (or at least one fiber segment) in the three dimensional structural network of fibers. This includes, but is not limited to drug-containing fibrous structures that extend over a length, width, and thickness greater than 1.5, or greater than 2, or greater than 2.5, or greater than 3, or greater than 3.5, or greater than 4 times the average thickness of at least one fiber (or at least one fiber segment) in the three dimensional structural network of fibers. It may be noted that the terms "three dimensional structural network of drug-containing fibers", "three dimensional structural network of fibers", "three dimensional structural network of one or more fibers", "three dimensional structural network of one or more drug-containing fibers", and "three dimensional network of fibers" are used interchangeably herein.

Moreover, as used herein, the terms "fiber", "fibers", "one or more fibers", "one or more drug-containing fibers", and "drug-containing fibers", are used interchangeably. They are understood as the drug-containing structural elements (or building blocks) that make up a three dimensional structural network of drug-containing fibers. Fibers can be either solid or plasticized. The terms "plasticized fiber" and "wet fiber" are used interchangeably herein. Plasticized and wet fibers are understood as viscous fibers with a viscosity of the order of the viscosity of the plasticized matrix from which they were formed.

A fiber has a length much greater than its width and thickness (e.g., the length of a fiber is much greater than its width and the length of a fiber is much greater than its thickness). In the present disclosure, a fiber is referred to as having a length greater than 2 times its width and thickness. This includes, but is not limited to a fiber length greater than 3 times, or greater than 4 times, or greater than 5 times, or greater than 6 times, or greater than 8 times, or greater than 10 times, or greater than 12 times the fiber width and thickness. In yet other embodiments that are included but not limiting in the disclosure herein, the length of a fiber may be greater than 0.3 mm, or greater than 0.5 mm, or greater than 1 mm, or greater than 2.5 mm.

Moreover, as used herein, the term "fiber segment" refers to a fraction of a fiber along the length of said fiber.

In the invention disclosed herein, fibers (or fiber segments) may be bonded, and thus they may serve as building blocks of "assembled structural elements" with a geometry different from that of the original fibers (or fiber segments). Such assembled structural elements include two-dimensional elements (or 2-dimensional structural elements), one-dimensional elements (or 1-dimensional structural elements), or zero-dimensional elements (or 0-dimensional structural elements).

As used herein, a two-dimensional structural element is referred to as having a length and width much greater than its thickness. In the present disclosure, the length and width of a two-dimensional structural element are greater than 2 times its thickness. An example of such an element is a "sheet". A one-dimensional structural element is referred to as having a length much greater than its width and thickness. In the present disclosure, the length of a one-dimensional structural element is greater than 2 times its width and thickness. An example of such an element is a "fiber". A zero-dimensional structural element is referred to as having a length and width of the order of its thickness. In the present disclosure, the length and width of a zero-dimensional structural element are no greater than 2 times its thickness. Furthermore, the thickness of a zero-dimensional element is less than 2.5 mm. Examples of such zero-dimensional elements are "particles" or "beads" and include polyhedra, spheroids, ellipsoids, or clusters thereof.

In the invention herein, any three dimensional structural framework comprising at least one structural element (e.g., a zero-dimensional, one-dimensional, or two-dimensional structural element) comprising an arrangement/assembly/assemblage of bonded fibers or bonded fiber segments is considered a three dimensional structural network of one or more fibers.

DETAILED DESCRIPTION OF THE INVENTION

Fibrous Dosage Forms

In the context of the invention herein, a fibrous dosage form is referred to a dosage form that is prepared from at least one fiber. Thus, as shown in the non-limiting schematics of FIG. 1, a fibrous dosage form 100 may comprise a drug-containing solid 101 having an outer surface 102 and an internal structure 104 contiguous with and terminating at said outer surface 102. The internal structure 104 may comprise a three dimensional structural network of one or more drug-containing fibers 110, 120, 130, 140, 150, 160, 170, 180. The fibers may further comprise fiber segments separated and spaced from adjoining fiber segments by free spacings, $\lambda_f$, which define one or more free spaces 105 in the drug-containing solid 101.

The fibers 110, 120, 130, 140, 150, 160, 170, 180 may be oriented (e.g., arranged or structured) in a variety of ways, ranging from random (e.g., disordered as shown in FIG. 1g) to partially regular (e.g., partially ordered) to regular (e.g., ordered or not random as shown in FIGS. 1a-1f). In a regular structure, the position and thickness of the one or more fibers are typically precisely controlled. Dosage forms comprising such precisely controlled structures enable precisely controlled, predictable, and consistent properties, and a greater range of properties. This is desirable for optimizing the dosage form towards a specific functionality, such as the drug release rate (or the concentration-time profile of drug in the blood plasma after ingestion of the dosage form), the dosage form's mechanical properties, etc.

Furthermore, as shown in FIG. 1, in some embodiments the three dimensional structural network of one or more fibers may comprise inter-fiber contacts (e.g., contacts between fibers and/or fiber segments), which by way of example but not by way of limitation can be point contacts (e.g., the contact area is a circle, an ellipse, etc. as schematically shown in FIGS. 1b and 1d) or line contacts (e.g., the contact area is a rectangle, etc. as schematized in FIGS. 1a, 1e and 1f). For further information related to point contacts and line contacts, see, e.g., K. L. Johnson, "Contact mechanics", Cambridge University Press, 1985.

Inter-fiber contacts may provide mechanical support to the fibrous structure (e.g., the three dimensional structural network of one or more fibers). They may, however, also hold up disintegration and dissolution of the fibrous structure upon immersion in a dissolution medium. Thus, in some embodiments the number of inter-fiber contacts, and/or at least one position of an inter-fiber contact, and/or a contact width of at least one inter-fiber contact are precisely controlled in the three dimensional structural network of one or more fibers.

Moreover, as shown in the non-limiting examples of three dimensional structural networks of fibers shown in FIGS. 1e and 1f, the fibers may be bonded to each other along a line contact to form one or more 2-dimensional structural elements (e.g., one or more sheets). In FIG. 1e, the fibrous structure comprises one such 2-dimensional structural element that is continuous (e.g., one continuous sheet) 150. In FIG. if the fibrous structure comprises a combination of fibers 160 and sheets 170.

Figure 2:
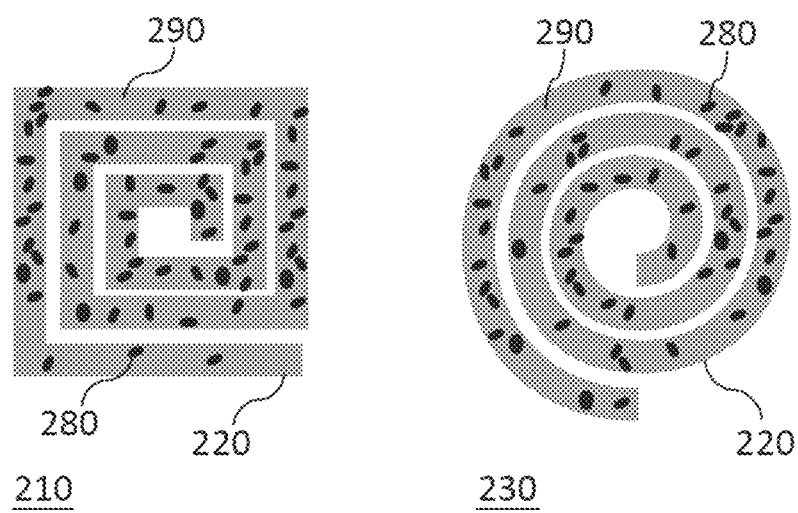
FIG. 2 shows additional schematic diagrams of microstructures of fibrous dosage forms according to this invention.

Other non-limiting examples of three dimensional structural networks of fibers are shown in FIG. 2, which presents a top view of fibers 220 in a plane forming a rectangular structure 210, as well as a top view of fibers 220 in a plane forming a circular (or elliptical) structure 230.

Additional non-limiting examples of fibrous structures can be found in the commonly owned references M. F. Ashby, "The mechanical properties of cellular solids", Metall. Trans. A, 14A (1983) 1755-1769; L. J. Gibson, M. F. Ashby, "Cellular solids: structure and properties", second edition, Cambridge University Press, 1999; L. J. Gibson, M. F. Ashby, "Cellular solids in medicine", second edition, Cambridge University Press, 1999. Moreover, further details related to fibrous dosage forms can be found in the U.S. patent application Ser. No. 15/482,776.

Any more examples of fibrous dosage forms or fibrous structures would be obvious to a person of ordinary skill in the art. All of them are within the scope of this invention.

Compositions

Typically, the compositions of the one or more solid or semi-solid fibers comprising the three dimensional structural network of fibers include at least one active ingredient. By way of example but not by way of limitation, said active ingredient may be selected from the group comprising acetaminophen, aspirin, caffeine, ibuprofen, an analgesic, an anti-inflammatory agent, an anthelmintic, anti-arrhythmic, antibiotic, anticoagulant, antidepressant, antidiabetic, anti-epileptic, antihistamine, antihypertensive, antimuscarinic, antimycobacterial, antineoplastic, immunosuppressant, antithyroid, antiviral, anxiolytic and sedatives, beta-adrenoceptor blocking agents, cardiac inotropic agent, corticosteroid, cough suppressant, diuretic, dopaminergic, immunological agent, lipid regulating agent, muscle relaxant, parasympathomimetic, parathyroid, calcitonin and biphosphonates, prostaglandin, radiopharmaceutical, anti-allergic agent, sympathomimetic, thyroid agent, PDE IV inhibitor, CSBP/RK/p38 inhibitor, or a vasodilator, among others.

In some embodiments, the one or more solid or semi-solid fibers comprising the three dimensional network of fibers further comprise at least one pharmaceutical excipient. Non-limiting examples of excipients include polyethylene glycol (PEG), polyethylene oxide, polyvinylpyrrolidone (PVP), PEG-PVP copolymer, poloxamer, lauroyl macrogol-32 glycerides, polyvinylalcohol (PVA), PEG-PVA copolymer, polylactic acid, polyvinylacetate phthalate, polymethacrylates (e.g., poly(methacrylic acid, ethyl acrylate) 1:1, or butylmethacrylat-(2-dimethylaminoethyl)methacrylat-methylmathacrylat-copolymer), gelatin, cellulose or cellulose derivatives (e.g., microcrystalline cellulose, hydroxypropyl cellulose, hydroxyethyl cellulose, methyl cellulose, hydroxypropyl methyl ether cellulose, hydroxypropyl methylcellulose, hydroxypropyl methylcellulose acetate succinate, hydroxypropyl methylcellulose phthalate, cellulose acetate phthalate, etc.), starch, polylactide-co-glycolide, polyvinyl caprolactam-polyvinyl acetate-polyethylene glycol graft copolymer, lactose, starch derivatives (e.g., pregelatinized starch or sodium starch glycolate, etc.), chitosan, pectin, polyols (e.g., lactitol, maltitol, mannitol, isomalt, etc.), acrylic acid crosslinked with allyl sucrose or allyl pentaerythritol (e.g., carbopol), sodium alginate, or polyacrylic acid, among others.

The one or more free spaces may be filled with a gas, or a liquid, or a solid, or nothing (e.g., a vacuum). Gases that may fill the one or more free spaces include, but are not limited to one of air, oxygen, argon, nitrogen, $CO_2$, nitric oxide, or helium, among others. Similarly, liquids to fill the one or more free spaces may be selected from the group comprising water, olive oil, Polyethylene glycol (PEG) with molecular weight smaller than about 1000 Da (e.g. PEG 400, PEG 300, etc.), Poloxamer 124, 2-Pyrrolidone, Glycerol triacetate (Triacetin), D-alpha tocopheryl polyethylene glycol 1000 succinate (TPGS), Polyoxyl Hydroxystearate, Polyoxyl 15 Hydroxystearate, Castor oil, Polyoxyl castor oil (Polyethoxylated castor oil), Polyoxyl 35 castor oil, Polyoxyl hydrogenated castor oil, Glyceryl monooeleate, Glycerin, Propylene glycol, Propylene carbonate, Propionic acid, Peanut oil, water, Sesame oil, Almond oil, combinations of such (and/or other) liquids with a polymer or any other molecule that dissolves in them, among others. In most cases, however, the one or more free spaces comprise air.

It may be noted that in the invention herein, the term "constituent" is referred to at least one component (e.g., at least one ingredient material) of the composition of the dosage form. Thus, a "solid constituent" comprises a solid form (e.g., a granular solid, sheet, rod, filament, etc.) of at least one component (e.g., at least one ingredient) of the dosage form's composition. Non-limiting examples of solid constituents are active ingredients and/or excipients.

Any more examples of the compositions of the one or more fibers and free spaces of the fibrous dosage forms would be obvious to a person of ordinary skill in the art. All of them are within the scope of this invention.

Solid Structures of Fibers

The solid structure of a fiber may comprise a single phase or multiple phases. A non-limiting example of a single-phase fiber is a drug-excipient solid solution (e.g., dissolved drug molecules in an excipient matrix). If a fiber consists of multiple phases, such as at least a drug phase and at least an excipient phase, the phases (e.g., the drug and excipient phases) may be structured in the fiber in an ordered or partially or completely disordered manner. The structural features of the individual phases may comprise any shape. This includes particles, beads, polygons, ellipsoids, cubes, tubes, rods, any combinations thereof, etc. The size (e.g., the length or diameter) of the structural features may be at the molecular, nano-, micro-, meso-, or macro-scale. By way of example but not by way of limitation, solid structures of fibers comprising drug particles that are embedded in an excipient matrix are included herein.

More such examples of solid structures of fibers would be obvious to a person of ordinary skill in the art. All of them are within the scope of this invention.

Aspects of the Method

Figure 3:
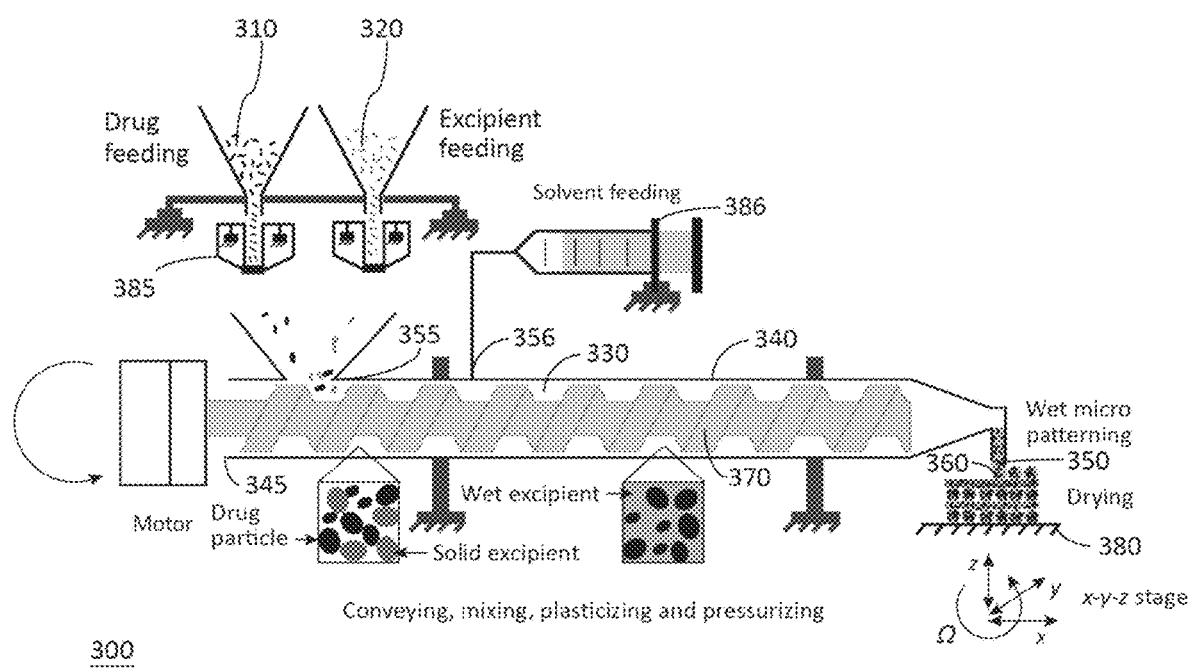
FIG. 3 is a schematic of a method and an apparatus for manufacturing fibrous dosage forms according to this invention.

FIG. 3 presents a non-limiting example of a method of manufacturing pharmaceutical solid dosage forms according to this invention. One or more drugs 310 and/or one or more solid excipients 320 (the one or more drugs 310 and/or one or more solid excipients 320 combined are also referred to herein as "one or more solid constituents") are injected into an extrusion channel 330 having a cross section extending along its length inside a housing 340. Also, at least one solvent that solvates at least one injected solid constituent is injected into the extrusion channel 330. The rate at which solvent is injected and the volume fraction of the at least one solvated solid constituent with respect to the total volume of the one or more injected solid constituents are so that the one or more injected solid constituents form a plasticized matrix upon contact and mixing with the solvent. The plasticized matrix is (subsequently or concurrently as it is formed) conveyed towards an exit port 350 of the extrusion channel 330 by applying mechanical work on the plasticized matrix (e.g., by applying a shear force on the plasticized matrix along a fraction of the extrusion channel 330, or by applying a pressure gradient in the direction of the extrusion channel 330, etc.). The plasticized matrix is then extruded through an exit port 350 to form at least one plasticized fiber 360. Subsequently, said at least one plasticized fiber 360 (e.g., one or more plasticized fibers) is/are structured to a three dimensional structural network of one or more fibers. In some embodiments, the three dimensional structural network of one or more fibers is then solidified by evaporating the solvent to form a fibrous dosage form with sufficient rigidity.

Figure 4:
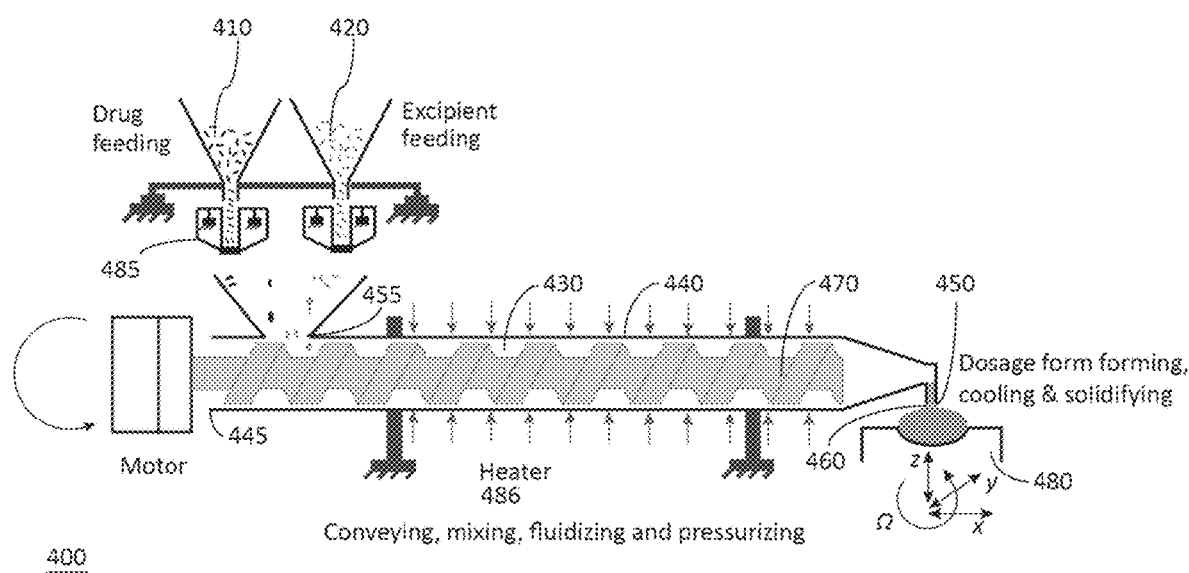
FIG. 4 is another schematic of a method and an apparatus for manufacturing fibrous dosage forms according to this invention.

Another non-limiting example of a method of manufacturing pharmaceutical solid dosage forms according to this invention is shown in FIG. 4. One or more drugs 410 and/or one or more solid excipients 420 (e.g., one or more solid constituents) are fed or injected into an extrusion channel 430 having a cross section extending along its length inside a housing 440. The injected one or more solid constituents are then heated to a temperature greater than the melting temperature of at least one injected solid constituent. Thus at least one injected solid constituent is fluidized (e.g., it transitions from solid or solid-like to fluidic or fluid-like) upon heating. The volume fraction of the fluidized solid constituent (or the fluidized solid constituents) with respect to the volume of the one or more injected solid constituents is so that the one or more injected solid constituents form a plasticized matrix upon heating (and mixing). The plasticized matrix is (subsequently or concurrently as it is formed) conveyed towards an exit port 450 of the extrusion channel 430 by applying mechanical work on the plasticized matrix (e.g., by applying a shear force on the plasticized matrix along a fraction of the extrusion channel 430, or by applying a pressure gradient in the direction of the extrusion channel 430, etc.). The plasticized matrix is then extruded through an exit port 450 to form at least one plasticized fiber 460. Subsequently, said at least one plasticized fiber 460 (e.g., one or more plasticized fibers) is/are structured to a three dimensional structural network of one or more fibers. In some embodiments, the three dimensional structural network of one or more fibers is then solidified by cooling it to a temperature below the solidification temperature.

Figure 5:
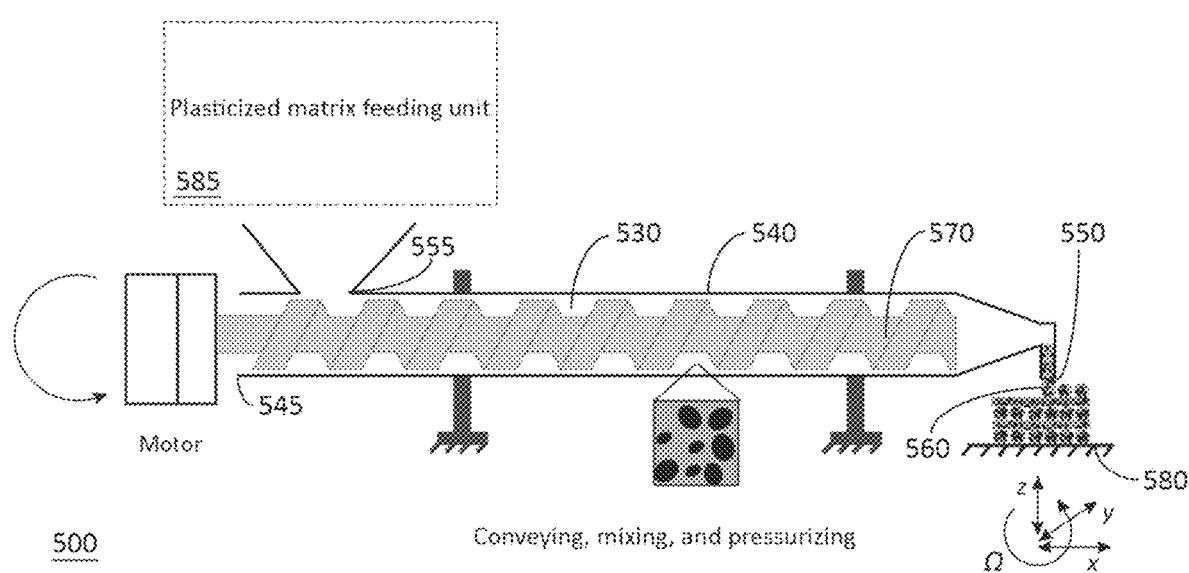
FIG. 5 is a further schematic of a method and an apparatus for manufacturing fibrous dosage forms according to this invention.

FIG. 5 presents another non-limiting example of a method of manufacturing pharmaceutical solid dosage forms according to the invention herein. At least one plasticized matrix is fed or injected into an extrusion channel 530 having a cross section extending along its length inside a housing 540. The plasticized matrix in the extrusion channel is then conveyed towards an exit port 550 of the extrusion channel 530 by applying mechanical work on the plasticized matrix (e.g., by applying a shear force on the plasticized matrix along a fraction of the extrusion channel 530, or by applying a pressure gradient in the direction of the extrusion channel 530, etc.). The plasticized matrix is then extruded through an exit port 550 to form at least one plasticized fiber 560. Subsequently, said at least one plasticized fiber 560 (e.g., one or more plasticized fibers) is/are structured to a three dimensional structural network of one or more fibers. In some embodiments, the three dimensional structural network of one or more fibers is then solidified to form a fibrous dosage form with sufficient rigidity.

It may be noted that in any example presented herein, the extrusion channel 330, 430, 530 may comprise one or multiple exit ports through which plasticized material can be extruded. Also, a three dimensional network of one or more fibers may be combined with other elements of a dosage form, such as one or more drug-containing solids, one or more solids that do not contain a drug, one or more coating shells, liquids, gases, etc. Furthermore, in the invention herein, the terms "plasticized fiber" and "fibrous extrudate" are used interchangeably. Moreover, any sequence of steps described in the invention herein may be performed concurrently (e.g., at least one step is performed at the same time as another step) or in sequence (e.g., one step is performed at a time and a subsequent step starts after completion of a previous step). In addition, any process step described with respect to one aspect of the invention can be applied with respect to another aspect. By way of example but not by way of limitation, a solid constituent may be plasticized by a combination of solvation and melting.

Any more examples of the process steps to manufacture the fibrous dosage forms would be obvious to a person of ordinary skill in the art. All of them are within the scope of this invention.

Process Models

The following non-limiting examples present ways by which specific non-limiting examples of the process and apparatus disclosed may be modeled. The models will enable one of skill in the art to more readily understand the invention and its features. The models and examples are presented by way of illustration, and are not meant to be limiting in any way.

(a) Process Overview

Figure 6:
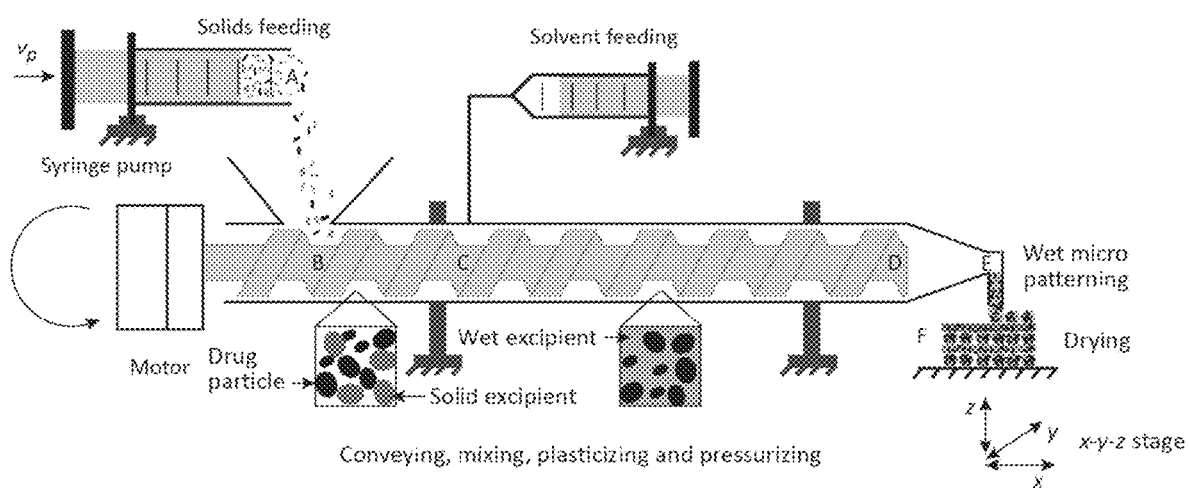
FIG. 6 presents a method and apparatus for manufacturing fibrous dosage forms according to a specific embodiment of the invention herein.

The models presented refer mostly to the non-limiting apparatus and method shown schematically in FIG. 6. One of the inputs is a mixture of solid drug and solid polymeric excipient at a predetermined drug-to-excipient mass ratio. The powder is filled in a syringe at point A. By controlled displacement of the piston, the powder mixture is fed (also referred to herein as "injected") through a hopper into an extrusion channel at B. The solid granules are then transported forward from B to C by the rotating screw. At point C a solvent, the other input, is added to the mixture, solvating the excipient and forming a plasticized mass.

The pressure of the plasticized material increases as it translates forward along the screw. The pressure at D should be large enough (at a required volumetric flow rate) to drive the semi-solid mass through a converging die to E, and through a cylindrical nozzle (e.g., an exit port) thereafter. The fibrous extrudate is then 3D-micro-patterned to a three dimensional network of one or more fibers (e.g., a dosage form structure) at F. Finally, the wet fibrous structure is dried to form a solid fibrous dosage form with sufficient strength and rigidity.

(b) Injecting Granular Solids into the Extrusion Channel

The mass flow rate, $dM_{sp}/dt$, at which solid particles (e.g., one or more granular solids) are injected into the extrusion channel is controlled volumetrically in the non-limiting example of FIG. 6. Thus $$\frac{dM_{sp}}{dt} = \rho_{sp}\phi_{sp}A_{sp}v_{sp} \tag{1}$$

where $\rho_{sp}$ is the density (or average density) of the solid particles, $\varphi_{sp}$ their volume fraction in the particle bed, $A_{sp}$ the cross-sectional area of the particle bed, and $v_{sp}$ its translational velocity. $v_{sp}$ is controlled by the axial velocity of a piston in the non-limiting example shown. Alternatively, $v_{sp}$ may be controlled by the rotation rate of a conveyor screw or other methods.

The mass flow rate of particulates in volumetric feeders is typically subject to some variation because the behavior of granular matter is not predictable. In Eq. (1), for example, $\varphi_{sp}$ is an experimental or statistical parameter that can be difficult to predict or control.

More precise control of the mass flow rate of particulates fed to the extrusion channel may be achievable, however, by gravimetric control. In a gravimetric particulate feeder, the mass flow rate of particulates injected is directly measured and controlled (e.g., the weight of the one or more granular solids injected into the extrusion channel per unit time is measured and controlled). Thus, despite the difficulties in modeling the flow and behavior of granular matter, fairly precise control of the rate at which particulates are fed into the extrusion channel is achievable.

Precise control of the rate at which granular solid is injected can be desirable, for example, if multiple granular solids are injected with multiple feeders, and each injected granular solid comprises a different composition. Precise control of the injection rates enables precise control of the composition (e.g., precise control of the mass fraction of each component in the extrusion channel or in the dosage form). Such precise control of the composition is a quality attribute of pharmaceutics.

The models and concepts presented above are not limiting. Any more models or examples for injecting one or more granular solids, one or more plasticized matrices, or even one or more solid filaments, sheets, rods, etc. into the extrusion channel would be obvious to a person of ordinary skill in the art. All of them are within the scope of this invention.

(c) Fluidizing at Least One Granular Solid in the Extrusion Channel

The input to the non-limiting process shown in FIG. 6 is a granular material, thus powder handling is unavoidable at the beginning. But because at least one of the injected granular solids transitions from solid or solid-like to fluidic or fluid-like upon contact with a solvent (e.g., water, acetone, dimethylsulfoxide, ethanol, ethyl acetate, etc.), said at least one granular solid may be fluidized by solvation or dissolution in the solvent. For a solid particle that absorbs solvent by diffusion, the time to fluidize said particle by solvation, $t_{solv}$, is roughly equal to the time the solvent molecules require to diffuse to the center. Thus if diffusion is Fickian, $$t_{solv} \cong \frac{R_{sp}^2}{D_{eff}} \quad (2)$$

where $R_{sp}$ is the radius of the particle and $D_{eff}$ the effective diffusivity of the solvent in the particle.

By way of example but not by way of limitation, if $R_{sp}$=25 μm, $D_{eff}$=3×10⁻¹⁰ m²/s (e.g., of the order of the effective diffusivity of water in Kollicoat IR), $t_{solv}$=2.1 s. Thus for a screw rotating at 5-500 rpm, if each particle is surrounded by the solvent almost immediately after the solvent is added, the one or more granular solids are converted to a wet, plasticized material at 5×2.1/60-500×2.1/60=0.18-18 times the pitch of the screw forward from the solvent-feeding position. A granular solid may therefore be plasticized by solvation in an apparatus or method as illustrated in FIG. 6, provided the length of section CD (or section CF) is greater than the length required to solvate the particles.

The concepts above are not limiting. By way of example but not by way of limitation, if the housing or a fraction thereof is heated, a small melt pool may form at about 2-4 times the pitch of the screw forward from the point where the housing temperature exceeds the melting temperature of at least one injected granular solid (see, e.g., C. G. Gogos, Z. Tadmor, "Principles of polymer processing", second edition, John Wiley & Sons, 2006). Thus, a granular solid may also be fluidized by melting (see, e.g., FIG. 4 for a non-limiting method and apparatus).

Any more examples or models to fluidize the one or more injected granular solids in the extrusion channel would be obvious to a person of ordinary skill in the art. All of them are within the scope of this invention.

(d) Applying Mechanical Work on the Plasticized Matrix in the Extrusion Channel

Figure 7:
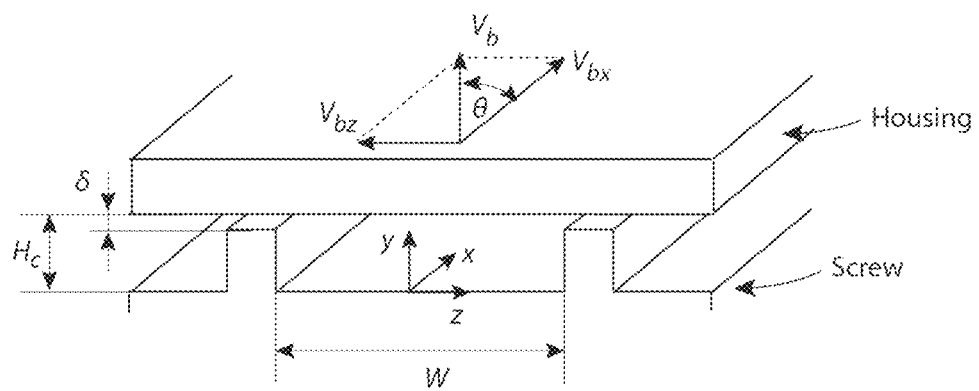
FIG. 7 illustrates a section of a rotating screw or conveying element inside a stationary, hollow housing.

In the non-limiting examples of FIGS. 6 and 7, mechanical work is applied on the plasticized material by a rotating screw. The screw transports the plasticized material forward along the extrusion channel and extrudes it through an exit port. The rotating screw may further contribute to mixing the plasticized material, degassing it, and so on. Thus, in the invention herein, the screw geometry and rotation rate may be adjusted to meet not only the requirements on flow rate and fluid pressure, but also to improve the uniformity, etc. of the plasticized material without compromising its chemical purity.

The concept described is again not limiting. By way of example but not by way of limitation, in some cases it may be desirable to apply mechanical work with a "twin" screw instead of a single screw. The "twin" screw is referred to herein as two parallel screws that can be co-rotating or counter-rotating. Furthermore, in some embodiments it may be desirable to combine one or more extrusion screws with one or more gear pumps or melt pumps. Moreover, mechanical work may be applied by the axial displacement of a piston in contact with the plasticized matrix, a peristaltic pump, or pressurized gas or liquid, among others.

For further models or examples, see, e.g., C. G. Gogos, Z. Tadmor, "Principles of polymer processing", second edition, John Wiley & Sons, 2006. Any more models or examples to apply mechanical work on the plasticized matrix in the extrusion channel so as to convey it towards an exit port, mix it, degas it, and so on would be obvious to a person of ordinary skill in the art. All of them are within the scope of this invention.

(e) Fluid Flow and Pressure Drop in the Extrusion Channel

Under steady-state conditions, the volumetric flow rate, Q, of the plasticized material in section CF is:

$$Q = \frac{1}{\rho}\left(\frac{dM_{sp}}{dt} + \rho_{solv}Q_{solv}\right) \quad (3)$$

where $\rho$ is the density of the plasticized material, and $\rho_{solv}$ the density and $Q_{solv}$, the volumetric feeding rate of the solvent. Under the conditions of the non-limiting experimental example 4 shown later in section "Further experimental and theoretical examples", $dM_{sp}/dt$=1.7 mg/s, $\rho_{solv}$=1000 kg/m³, $Q_{solv}$, =1.13 mm³/s, and $\rho$=1000 kg/m³. Thus, by Eq. (3) Q=2.83 mm³/s.

Figure 25:
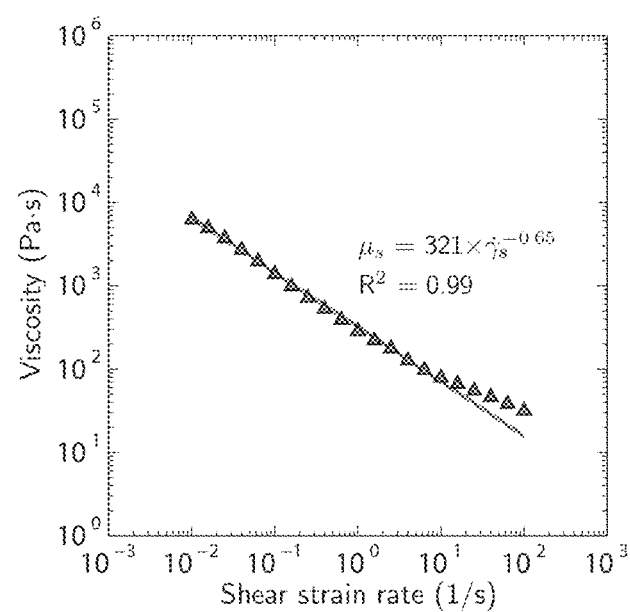
FIG. 25 presents the shear viscosity of a drug-excipient-water suspension versus shear strain rate. The composition of the suspension was: 36 wt % drug, 24 wt % excipient, and 40 wt % water. Polyvinyl alcohol-polyethylene glycol graft copolymer 3:1 with a molecular weight of 45,000 Daltons (tradename: Kollicoat IR) was the excipient and ibuprofen was the drug.

At this flow rate, for the geometry of the extrusion channel and the material of the non-limiting examples 2, 4, 10, and 11 shown later in section "Further experimental and theoretical examples", the Reynolds number, Re<1 and the Capillary number, Ca>1. Thus, inertial and capillary forces are small compared with the viscous forces. If the plasticized material is non-Newtonian viscous as shown in FIG. 25, its shear viscosity may be expressed by the following power law:

$$\mu_s = m\dot{\gamma}_s^{n-1} \quad 0.01 \text{ s}^{-1} \leq \dot{\gamma}_s \leq 100 \text{ s}^{-1} \quad (4)$$

where m and n are constants, and $\dot{\gamma}_s$ is the shear rate applied.

Figure 8:
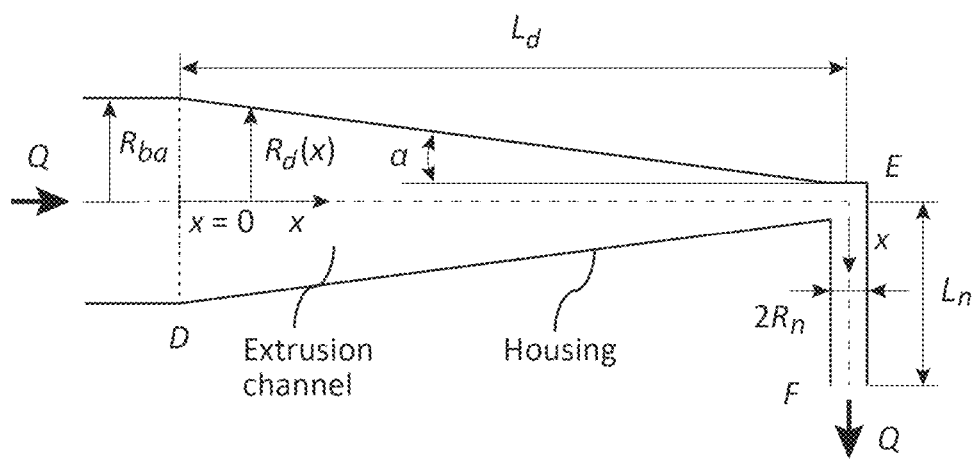
FIG. 8 is a schematic of a tapered fraction of an extrusion channel and an exit port.

FIG. 8 shows a non-limiting example of the extrusion channel near the exit port. The channel terminates into an exit port and tapers down before said exit port (e.g., it comprises a converging die and cylindrical nozzle through which the plasticized material can be extruded). For small taper angles the pressure gradient may be adapted from the solution to the mass- and momentum-balance equations in a circular tube with constant radius to give the following term for the pressure drop, $\Delta p$, from D to F:

$$\Delta p = \frac{2(1/n+3)^n mQ^n}{3\pi^n n \tan\alpha}\left(\frac{1}{R_n^{3n}} - \frac{1}{R_{ba}^{3n}}\right) + \frac{2(1/n+3)^n mQ^n L_n}{\pi^n R_n^{3n+1}} \quad (5)$$

where $R_{ba}$ is the inner radius of the extruder barrel, $\alpha$ the angle of the taper (here $\tan\alpha \approx (R_{ba}-R_n)/L_d$), $L_d$ the length of the converging die, $R_n$ the radius of the nozzle at the exit, and $L_n$ the length of the nozzle of the extrusion channel with constant diameter (FIG. 8).

By way of example but not by way of limitation, if $\alpha=10.75°$, $n=0.35$, $m=321$ Pa·s$^n$, $R_n=250$ µm, $R_{ba}=5$ mm, $Q=2.83$ mm$^3$/s, and $L_n=5$ mm, the estimated pressure drop $\Delta p=0.12$ MPa. This pressure can be developed by an apparatus as shown in FIG. 6. Furthermore, measuring $\Delta p$ provides a means for monitoring the flow rate and viscosity (the constants m and n) of the plasticized material during processing.

For further models or examples of fluid flow and pressure drop in a channel, see e.g., R. B. Bird, W. E. Stewart, E. N. Lightfoot, "Transport phenomena", 2$^{nd}$ edn., John Wiley & Sons, 2002. Any more examples of models of the fluid flow and pressure drop (or pressure gradient) in the extrusion channel would be obvious to a person of ordinary skill in the art. Moreover, further models or examples of extruding a plasticized matrix through an exit port to form a plasticized fiber would be obvious to a person of ordinary skill in the art. All such models and examples are within the scope of this invention.

(f) Kinematics of 3D-Micro-Patterning

The fibrous extrudate is then patterned on a substrate along a deterministic path set by the relative motion of the substrate to the exit port. In the invention herein, the terms "patterning", "micro-patterning", "depositing", "3D-micro-patterning", and "3D-patterning", are used interchangeably. Furthermore, the term "substrate" is referred to a material having a surface on which one or more fibers can be deposited. This includes, but is not limited to a stage (e.g., a working platform on which the fibers can be deposited but which is not part of the dosage form), a deposited fiber bed (which may or may not be part of the dosage form), a biocompatible film or solid material (which may or may not be part of the dosage form), a coating shell, etc.

Figure 9:
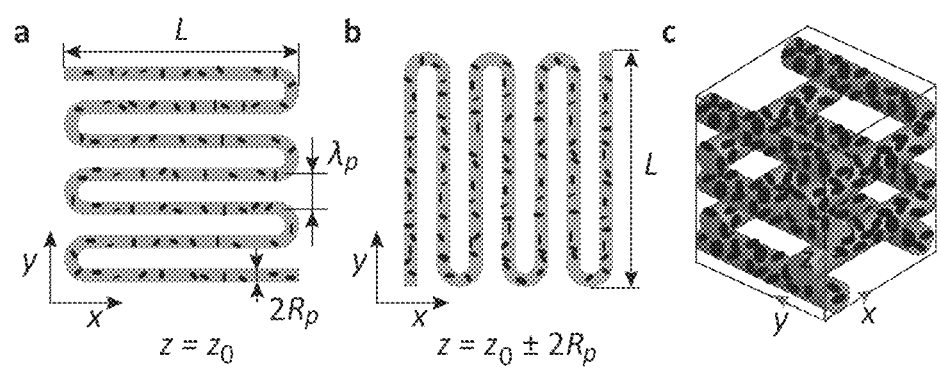
FIG. 9 illustrates a patterned microstructure of a fibrous dosage form: (a) top view of the fibers in the plane $z=z_0$, (b) top view of the fibers in the plane $z=z_0 \pm 2R_p$, and (c) isometric view of the microstructure.

In the non-limiting example of FIG. 6, the fibrous extrudate is patterned layer-by-layer along a deterministic path set by a moving x-y-z stage. The fiber segments in any layer are unidirectional, but are perpendicular to the fiber segments in the layers above and below, as shown in FIGS. 9a-c. During micro-patterning, the substrate (or stage) velocity in the x-y plane, $v_{st}$, is about equal to the velocity of the fibrous extrudate to avoid buildup or breakage of the fiber. Thus the time to micro-pattern the dosage form structure, $\tau_m$, is about the ratio of the length of the fiber in the micro-patterned structure, $L_p$, and the stage or stream velocity:

$$\tau_m = \frac{L_p}{v_{st}} = \frac{\pi R_p^2 L_p}{Q} \quad (6)$$

where $R_p$ is the radius of the plasticized fiber or fibrous extrudate and $$L_p = n_{fl} \times \frac{L^2}{\lambda_p} \quad (7)$$

where $n_{fl}$ is the number of fibrous layers in the dosage form (along the z-axis), L the side length of a (square) layer, and $\lambda_p$ the inter-fiber spacing.

By way of example but not by way of limitation, if $R_p=250$ µm, $\lambda_p=900$ µm, $L=10$ mm, and $n_{fl}=10$, $v_{st}=Q/\pi R_f^2=14.4$ mm/s and $L_p=1.11$ m. Thus the time to micro-pattern a dosage form, $\tau_m$, is 77 s in this case.

It may be obvious to a person of ordinary skill in the art that faster process rates can be achieved by increasing the stage velocity (e.g., the velocity at which the fiber exits the exit port) and by increasing the number of exit ports through which a plasticized matrix can be extruded to form one or more plasticized fibers. Moreover, the path of the substrate (e.g. the pattern produced) can be changed from one patterned layer to another. This enables, for example, to change the microstructure from one manufactured dosage form to another. More examples or models of the kinematics of 3D-micro-patterning would be obvious to a person of ordinary skill in the art. All of them are within the scope of this invention.

(g) Viscous Deformation of Micro-Patterned Fibers

For increasing the rigidity of the structure, the deposited fibers are desired to bond to the fibers below and above by viscous deformation. However, if the fibers deform too much and merge before they are dried, the fibrous pattern is lost and the structural integrity of the dosage form is compromised. Thus, the deformation rate of the fibers at and between the contacts may be appropriately controlled.

The viscous deformation problem may be described analogous to the corresponding linear elastic problem, provided the viscosity is Newtonian. The viscosity of the solvated mass of the non-limiting examples 4 and 9-13 is non-linear (as shown in FIG. 25 later), but in a small strain rate range the shear viscosity, $\mu_s$, may be approximated as the viscosity at the mean strain rate, $\mu_{s,m}$. Thus, if the fiber material is assumed Newtonian viscous and incompressible, the viscous deformation may be estimated from the corresponding linear elastic solution by replacing the elastic modulus, E, with $3\mu_{s,m}$ and integrating over time.

Figure 10:
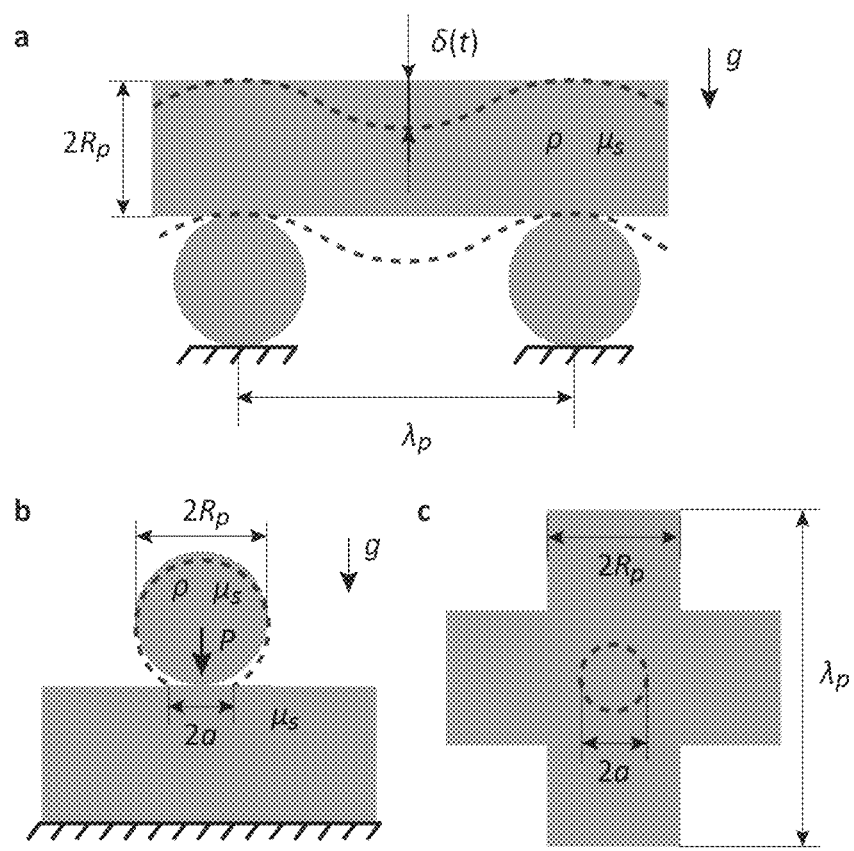
FIG. 10 is a schematic illustrating deformation of fibers during or after micropatterning: (a) a fiber bending downwards, (b) front view of the deformation at the contact of crossed fibers, and (c) top view of the deformation at the contact of crossed fibers.

FIG. 10a schematically shows a viscous fiber that bends downward between the contacts due to gravity. For small deflections, the maximum deflection, $\delta$, may be estimated from the solution of the corresponding elastic beam bending problem. Because the fiber is fixed at both ends, $$\delta = \int_0^t \frac{q\lambda^4}{1152\mu_{s,m}I}dt = \frac{\rho g \lambda_p^4 t}{288\mu_{s,m}R_p^2} \quad (8)$$

where the fiber weight per unit length, $q=\pi R_p^2 \rho g$, and the moment of inertia of the fiber cross-section, $I=\pi R_p^4/4$. By way of example but not by way of limitation, for $\mu_{s,m}=6220$ Pa·s, $R_p=250$ µm, $\lambda_p=900$ µm, and $\rho=1000$ kg/m$^3$, $\delta=2.5$ µm after $t=\tau_d=43.5$ s era is the drying time constant estimated in the non-limiting example 5 shown later in section "Further experimental and theoretical examples"). Thus, $\delta/\lambda_p=0.003\ll1$; bending does neither contribute to bonding nor distort the initial microstructure in this non-limiting example.

FIGS. 10b and 10c schematically illustrate the contact between two crossed cylindrical fibers. Analogous to the contact of a sphere on a flat plate, the contact area of crossed cylinders may be considered circular. If the contact radius, $a\ll R_p$, the radius of the plasticized fiber, the adapted form of the linear elastic solution is:

$$a^3 = \int_0^t \frac{3PR_p}{8\mu_{s,m}} dt \quad (9)$$

where t is the time after initiation of the contact and P the contact load (the weight of the fibers of length $\lambda_p$ above the plasticized contact). Thus $$P=\pi R_p^2 \lambda_p \rho g n_p \quad (10)$$

where $n_p$ is the number of fibers above the plasticized contact and g the acceleration due to gravity.

Combining Eqs. (9) and (10) gives:

$$a = \left(\frac{3\pi\rho g R_p^3 \lambda_p n_p t}{8\mu_{s,m}}\right)^{1/3} \quad (11)$$

By way of example but not by way of limitation, for $\mu_{s,m}=1035$ Pa·s, $\rho=1000$ kg/m³, $R_p=250$ μm, $\lambda_p=900$ μm, t=15 s, and $n_p\leq2$, by Eq. (11) $a\leq171$ μm. The calculated contact radius is 68% of the radius of the plasticized fiber in this non-limiting example. Thus, fiber bonding and structural integrity are assured.

It may be noted, however, that the assumption $a\ll R_p$ is not quite valid at the large strains estimated. Furthermore, the viscosity of the fibers is time- and space-dependent as solvent evaporates. The above analysis must therefore be considered highly approximate.

Nonetheless, it is readily seen from Eqs. (4), (5), (8), and (11) that a critical parameter to ensure that the plasticized formulation is shapeable to a fiber that bonds to the fibers below, but the micro-patterned structure deforms slowly during drying, is the viscosity of the wet fiber. By way of example but not by way of limitation, the viscosity of the wet fiber can be controlled by the solvent weight fraction. Thus the solvent weight fraction should be large enough to allow bonding of the micro-patterned fibers to each other. But if the solvent weight fraction is too large, the micro-patterned structure deforms excessively before the solvent is removed and the fibrous microstructure is lost.

Further models of the deformation of fibers at the contact can be found, for example, in K. L. Johnson, "Contact mechanics", Cambridge University Press, 1985. For models of bending of beams between contacts, see e.g., J. M. Gere, S. P. Timoshenko, "Mechanics of Materials", fourth edn., PWS Publishing Company, 1996. Any more models or examples of the deformation of plasticized fibers in a micro-patterned fibrous structure would be obvious to a person of ordinary skill in the art. All of them are within the scope of this invention.

(h) Drying of a Single Fiber

After micro-patterning, the solvent is removed from the fibers. A rigorous analysis of solvent evaporation from a plasticized polymeric fiber is a coupled diffusion-convection problem, which should account for structural changes of the polymer-solvent system due to solvent evaporation. Such an analysis requires the use of numerical methods and is well beyond the scope of this disclosure.

Figure 11:
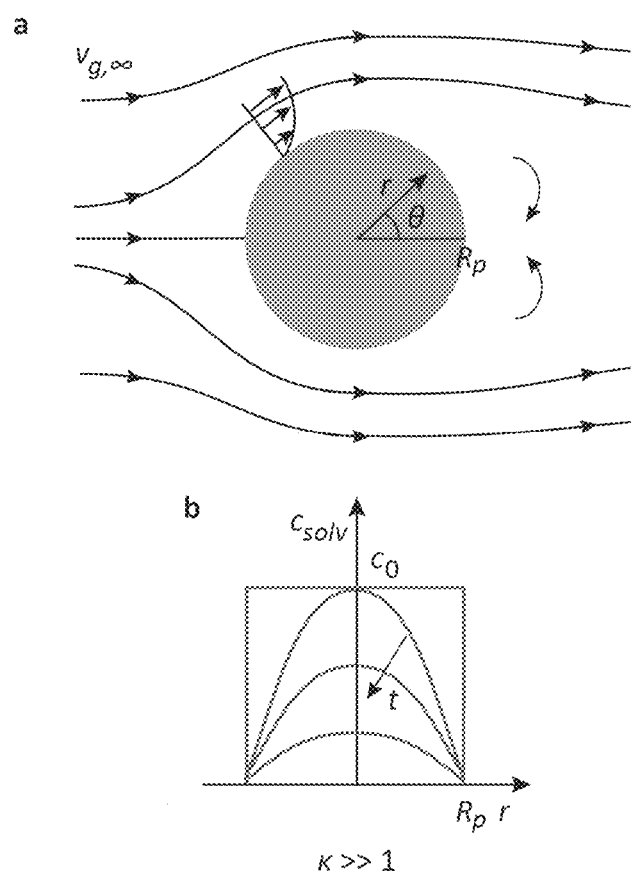
FIG. 11 schematically illustrates drying of a single fiber in convection: (a) streamlines of air flow around the fiber if $Re \approx 60$, and (b) solvent concentration profiles in the fiber if solvent removal is limited by diffusion through the fiber.

The aim here is modest in that it is to derive a rough solution for making engineering decisions. For the configuration shown in FIG. 11a, if the fiber radius is assumed invariant and solvent diffusion in the polymer is Fickian with constant solvent diffusivity, $D_{solv}$, the solvent concentration in the plasticized fiber, $c_{solv}$, is governed by:

$$\frac{\partial c_{solv}}{\partial t} = D_{solv} \frac{\partial^2 c_{solv}}{\partial r^2} \quad (12)$$

Because the solvent evaporates from the fiber surface and the concentration of solvent in the gas (e.g., air, nitrogen, argon, $CO_2$, etc.) far away from the fiber, $c_{g,\infty}$, is zero, the boundary condition at $r=R_p$ is:

$$-D_{solv}\frac{\partial c_{solv}}{\partial r} = k_c(c_g - c_{g,\infty}) \cong k_c \frac{p_{sat}}{\rho_{solv}} \frac{M_w}{RT} c_{solv} = k_{eff} c_{solv} \quad r = R_p \quad (13)$$

where $k_c$ is the convective mass transfer coefficient, $c_g$ the concentration of solvent in the gas, $p_{sat}$ the saturation vapor pressure of the solvent in air, $M_w$ the solvent's molecular weight, R the universal gas constant, T the temperature, and $k_{eff}$ the effective convective mass transfer coefficient.

The convective mass transfer coefficient, $k_c$, is a function of the Sherwood number, Sh, the diffusivity of the solvent molecules in the gas phase, $D_g$, and the fiber radius, $R_p$, as:

$$k_c = Sh \frac{D_g}{2R_p} \quad (14)$$

Assuming that the concentration profile is axially symmetric, the Sherwood number may be written as:

$$Sh = C_1 Re^{m_1} Sc^{1/3} \quad (15)$$

where $C_1$ and $m_1$ are empirical parameters, the Reynolds number, $Re=2\rho_g v_{g,\infty} R_p/\mu_g$, and the Schmidt number, $Sc=\mu_g/\rho_g D_g$ ($\rho_g$ is the density of the gas, $v_{g,\infty}$ its far-field velocity, and $\mu_g$ its viscosity).

Thus for the non-limiting example of a wet fiber with water as solvent that is dried with air at 60° C., $v_{g,\infty}=2.3$ m/s, and atmospheric pressure, the Reynolds number, $Re\approx60.75$, the constants $C_1\approx0.62$ and $m_1\approx0.47$, and by Eqs. (14) and (15), $k_c=0.23$ m/s.

If $k_c$ and $D_{solv}$ are known, an analytical solution of the solvent concentration in the fiber can be found as [28]:

$$\frac{c_{solv} - c_0}{c_0} = 1 - \sum_{i=1}^{\infty} \frac{2\kappa J_0(r\beta_i/R_p)}{(\beta_i^2 + \kappa^2)J_0(\beta_i)} \exp(-\beta_i^2 D_{solv} t / R_p^2) \quad (16)$$

where $c_0$ is the initial concentration of solvent in the fiber, the $\beta_i$'s are the roots of $$\beta J_1(\beta) - \kappa J_0(\beta) = 0 \quad (17)$$

($J_1$ and $J_0$ are the Bessel functions of the first kind) and $\kappa$ is a dimensionless measure of the ratio of the mass transfer resistances inside and at the surface of the fiber:

$$\kappa = \frac{k_{eff} R_p}{D_{solv}} = \frac{p_{sat} M_w}{\rho_{solv} RT} \frac{k_c R_p}{D_{solv}} \tag{18}$$

By way of example but not by way of limitation, for $p_{sat}$=20 kPa, $M_w$=18 g/mol, $\rho_{solv}$=1000 kg/m³, T=333 K, $k_c$=0.23 m/s, $R_p$=250 µm, and $D_{solv}$=2.5×10⁻¹⁰ m²/s, $\kappa$=29.5>>1. Thus, the evaporation rate is mostly limited by the diffusive flux of solvent in the fiber in this case, and the solvent concentration profile may be roughly as shown schematically in FIG. 11b.

The ratio of the mass of solvent in the fiber at time t, M(t), to the mass at t=0, $M_0$, may then be approximated by an adapted form of the equation presented by Crank:

$$\frac{M(t)}{M_0} = \sum_{i=1}^{\infty} \frac{4 \exp(-\beta_i^2 D_{solv} t / R_p^2)}{\beta_i^2} \tag{19}$$

From the graphical solution given by Crank, 98 percent of the solvent is removed if $D_{solv} t / R_p^2 \approx 0.77$. The drying time may therefore be written as:

$$\tau_{0.98} = 0.77 \frac{R_p^2}{D_{solv}} \tag{20}$$

By way of example but not by way of limitation, if $R_f$=250 µm and $D_{solv}$=2.5×10⁻¹⁰ m²/s, by Eq. (20) $\tau_{0.98}$=193 s. The drying time is comparatively short because of the large specific surface area of the thin fibers.

Further models of the diffusion of solvent through polymers can be found, for example, in J. Crank, "The mathematics of diffusion", second edition, Oxford University Press, 1975; and in J. Crank. G. S. Park, "Diffusion in polymers", Academic Press, 1968. Moreover, it may be obvious to a person of ordinary skill in the art that diffusion limited evaporation may be achieved at lower temperatures and gas velocities by reducing the pressure of the gas. Any more models or examples of drying of plasticized fibers would be obvious to a person of ordinary skill in the art. All of them are within the scope of this invention.

(i) Drying of a fibrous dosage form

Figure 12:
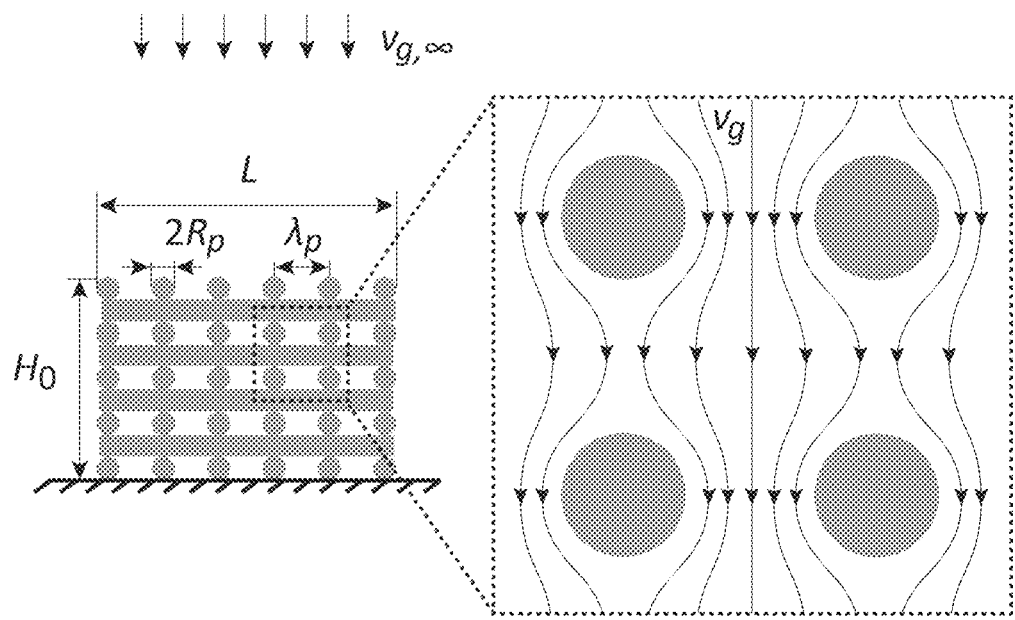
FIG. 12 presents a non-limiting schematic of streamlines of gas flow around the fibers of a fibrous dosage form in viscous or creeping flow.
Figure 13:
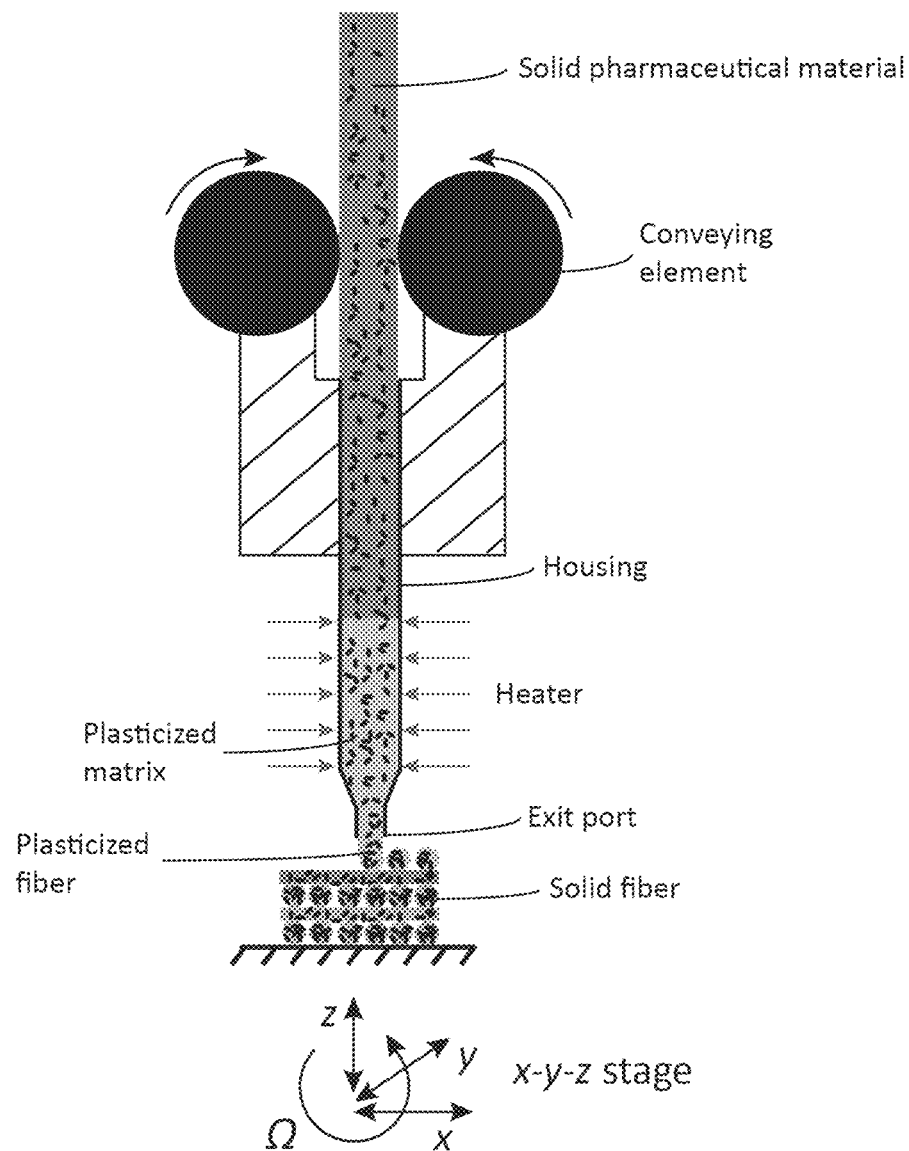
FIG. 13 presents a further non-limiting schematic of an apparatus and method for manufacturing fibrous dosage forms according to this invention.

Within the fibrous dosage form structure, the velocity of the dry air stream around the fibers cannot be determined by analytical methods. An approximation may, however, be obtained for a system where the flow in the interior is dominated by viscous forces. The streamlines around the fibers in the structure may be as shown in FIG. 12 in this case. The average fluid velocity in the open spaces in the direction of flow, $\bar{v}_g$, may then be approximated by Darcy's law:

$$\bar{v}_g = \frac{1}{1 - \phi_p} \frac{K}{\mu_g} \frac{dp_g}{dx} \tag{21}$$

where K is the hydraulic permeability and $dp_g/dx$ the gas pressure gradient across the fibrous structure.

The hydraulic permeability may be estimated by the Kozeny-Carman equation:

$$K = \frac{1}{k} \frac{(1 - \phi_p)^3}{A_v^2} \tag{22}$$

where the volume fraction of plasticized fibers in the structure, $$\phi_p \cong \frac{\pi R_p}{2 \lambda_p} \tag{23}$$

and the surface area of fibers per unit volume of the dosage form, $A_v = \pi/\lambda_p$. The Kozeny constant, $k \approx 5$ (for $\varphi_p \approx 0.44$).

An estimate of the pressure gradient in the direction of gas flow through the fibrous structure is:

$$\frac{dp_g}{dx} \cong \frac{\rho_g v_{g,\infty}^2}{L} \tag{24}$$

where $v_{g,\infty}$ is the far-field velocity of the gas.

Thus by way of example but not by way of limitation, if $v_{g,\infty}$=2.3 m/s, $\rho_g$=1.06 kg/m³, $\mu_g$=2×10⁻⁵ Pa·s, L=10 mm, $\varphi_p$=0.44, and $A_v$=3490 m⁻¹ are inserted in Eqs. (21)-(24), the average gas velocity in the pores, $\bar{v}_g$=0.1 m/s. Assuming that the maximum velocity in the pores is a factor two greater than the average velocity (i.e., $v_{g,max}=2v_g$=0.2 m/s), the Reynolds number of the gas flow around a fiber in the dosage form, Re=$2\rho_g v_{g,max} R_p / \mu_g$=7.7. At such Reynolds numbers, the boundary layer separates behind the fibers and thus the viscous flow assumption (and Darcy's law) must be considered highly approximate.

Nonetheless, the estimated value of the Reynolds number may be inserted in Eq. (15), and then the convective mass transfer coefficient estimated by Eq. (14). For the non-limiting parameter values given above and in section (h), $k_c$=0.1 m/s and $\kappa$=13.5>>1, provided the solvent concentration in the free spaces of the internal structure is small. Thus, under the non-limiting conditions presented, the drying time of the fibers in the fibrous structure is limited by the diffusion of solvent through the fibers, too, and may be approximated by Eq. (20).

Further models for estimating the gas velocity in the fibrous structure can be found, for example, in J. Happel and H. Brenner, "Low Reynolds number hydrodynamics with special application to particulate media", Prentice-Hall, Englewood Cliffs, N.J., 1965. Any more models or examples of drying of fibrous structures would be obvious to a person of ordinary skill in the art. All of them are within the scope of this invention.

(k) Contraction of Fibers During Drying

As the solvent is removed upon drying, the fibers may contract both radially and axially. If the fibers can be assumed ideal solutions (i.e., the solid and liquid volumes are conserved upon drying), the ratios of radius and inter-fiber distance of the solid fibers to the corresponding values of the plasticized fibers, in isotropic contraction, are:

$$\frac{R_s}{R_p} = \frac{\lambda_s}{\lambda_p} = \left(1 - \frac{c_0}{\rho_{solv}}\right)^{1/3} \tag{25}$$

where $c_0$ is the concentration of solvent in the plasticized fibers before drying. By way of example but not by way of limitation, if $c_0/\rho_{solv}$=0.4, $R_s/R_p$=$\lambda_s/\lambda_p$=0.84.

(l) Summary of Models

The above models illustrate the effects of the design of the apparatus, the properties of the input material, the microstructural parameters of the dosage form, the properties of the plasticized material, and additional process, design, and material parameters (e.g., the screw rotation rate, screw geometry, the drying conditions, etc.) on the process time, microstructure, and composition of the fibrous dosage forms. The process time is short because the small excipient particles can be solvated in a few seconds, and the dosage form micro-patterned and dried in about a minute or even less. Furthermore, the patterned microstructure is well preserved, and the fibers are bonded to their neighbors, if the viscosity of the plasticized fibers is controlled. Thus, the above models demonstrate that fibrous dosage forms with deterministic microstructure can be economically manufactured.

It may be obvious to a person of ordinary skill in the art that many more process examples and models could be developed and presented. All the examples and models which after reading this specification carefully are obvious to a person of ordinary skill in the art are within the spirit and scope of this invention.

Elements of the Method, Apparatus, and Dosage Form

In view of the theoretical considerations and examples above, which are suggestive and approximate rather than exact, the aspects and embodiments of the present invention may further include the following elements.

In any aspect of the method, apparatus, or dosage form disclosed herein, the geometry of the extrusion channel cross section can assume any shape, and thus may be circular, elliptical, polygonal, combinations thereof, and so on. Furthermore, the extrusion channel cross section may be uniform or non-uniform along its length. Thus, in some embodiments the extrusion channel cross section tapers down before an exit port to the cross section of said exit port. Moreover, in some embodiments the extrusion channel bifurcates into at least one other end comprising an exit port. Multiple exit ports are desirable for achieving high process rates.

In any aspect of the invention herein, the extrusion channel may be equipped with valves to control the flow rate of plasticized material through it. By way of example but not by way of limitation, a valve may stop the flow of plasticized material through an exit port or it may direct the flow of plasticized material through specific regions of the extrusion channel.

In any aspect of the invention herein, the housing may have multiple feeding ports for injection solid material, liquid material, plasticized material, etc. into the extrusion channel.

In some embodiments herein, a fraction of the housing may be optically transparent. A partially or entirely optically transparent housing may enable improved optical sensing of the state or structure of the material (e.g., one or more solid constituents or a plasticized matrix) in the extrusion channel. Non-limiting examples of materials which an optically transparent fraction of the housing may consist of include one of glass (e.g., silicon dioxide, borosilicate, alumina, germanium dioxide, spectrosil quartz, etc.) or plexiglass (e.g., poly(methyl methacrylate)).

In some embodiments, the housing or a fraction thereof is non-optically-transparent. Non-limiting examples of non-optically-transparent materials which the housing may consist of include one of metals (e.g, various forms of steel, stainless steel, iron, chromium, aluminum, tungsten, iridium, nickel, platinum, copper, any alloys or combinations thereof, etc.) or one of polymers, such as polyethylene, polypropylene, polystyrene, polycarbonate, acrylonitrile butadiene styrene, and so on.

In the invention herein, a conveying element comprises a device for applying mechanical work on a solid (e.g., a granular solid, filament, sheet, etc.) or a fluid (e.g., a plasticized matrix, liquid, etc.) to transport said solid or fluid towards an exit port of the extrusion channel. A non-limiting example of a conveying element is a screw. A screw may, for example, comprise multiple sections with different geometries for performing specific functions or steps (e.g., transporting a granular solid towards an exit port, transporting a plasticized matrix towards an exit port, mixing drug and excipient, mixing excipient and solvent, and so on). Furthermore, a screw may perform specific functions or steps concurrently. Thus, a screw allows to integrate multiple functions or steps into a continuous, steady process. A screw may operate as 'single screw' or within an arrangement of multiple screws, such as 'twin screws'. Other non-limiting examples of conveying elements include fluid pumps (e.g., extrusion gear pumps, melt pumps, peristaltic pumps, diaphragm pumps, rotary vane pumps, etc.), pistons, and so on. Any conveying element may be operated with at least one motor (e.g., an electrical AC motor, DC motor, stepper motor, etc.), or with at least one hydraulic actuator, or with at least one pneumatic actuator, among others.

The apparatus or method disclosed herein may further comprise at least one solids feeding unit for injecting at least one solid constituent into the extrusion channel. By way of example but not by way of limitation, a solids feeding unit may comprise a device that is capable of controlling the rate at which a solid constituent is injected into the extrusion channel, such as one or more rotating screws inside a barrel, at least one translating piston inside a barrel, and so on. The injection rate may, for example, be controlled volumetrically or gravimetrically. A solids feeding unit may operate in a continuous (e.g., a solid constituent is continuously injected into the extrusion channel), semi-continuous, or batch mode (e.g., specific volumes or masses of a solid constituent are injected into the extrusion channel at specific times). Any more examples of solids feeding units, or how solids feeding units may be operated, would be obvious to a person of ordinary skill in the art. All of them are within the scope of this invention.

In some embodiments, a fraction of (or all) the input material is supplied to the extrusion channel in the form of a plasticized matrix. Thus, the apparatus or method disclosed herein may further comprise at least one plasticized matrix feeding unit for feeding or injecting a plasticized matrix into the extrusion channel. By way of example but not by way of limitation, said plasticized matrix feeding unit may comprise a device that is capable of controlling the rate at which a plasticized matrix is injected into the extrusion channel, such as one or more rotating screws inside a barrel, at least one translating piston inside a barrel, and so on. The injection rate may, for example, be controlled volumetrically or gravimetrically. Also a plasticized matrix feeding unit may be operated in a continuous (e.g., a plasticized matrix is continuously injected into the extrusion channel), semi-continuous, or batch mode (e.g., specific volumes of a plasticized matrix are injected into the extrusion channel at specific times). Any more examples of plasticized matrix feeding units, or how plasticized matrix feeding units may be operated, would be obvious to a person of ordinary skill in the art. All of them are within the scope of this invention.

In any aspect herein, an active ingredient or an excipient may be injected into the extrusion channel as a solid material (e.g., a granular solid, filament, rod, etc), as a liquid material, as a plasticized material, as dissolved molecules in a liquid solvent, and so on.

In some embodiments, at least one input constituent is solid but plasticizes by solvation upon contact with a suitable solvent. The term "input constituent is referred to herein as a constituent that is injected into the extrusion channel. Furthermore, the terms "plasticize" or "plasticizing" and "fluidize" or "fluidizing" are used interchangeably herein. Moreover, in the context herein a solid constituent that plasticizes by solvation upon contact with a suitable solvent (e.g., a solid constituent that solvates upon contact with a suitable solvent) is referred to a solid constituent having a viscosity that decreases upon contact with a suitable solvent. Typically, a solid constituent may be considered plasticized as soon as its viscosity has decreased so much that it is of the order of or smaller than the viscosity of a plasticized matrix. Non-limiting solid constituents that plasticize by solvation include solid constituents that transition from solid to semi-solid upon contact with a solvent, solid constituents that transition from solid to liquid upon contact with a solvent, solid constituents that exhibit a gradual decrease in viscosity upon contact with a solvent, solid constituents that transition from solid to a plasticized matrix upon contact with a solvent, solid constituents that partially or entirely dissolve in a substantial volume of a suitable solvent, and so on.

Thus, to form a plasticized matrix by solvating at least one injected solid constituent, the apparatus disclosed herein may further comprise at least one solvent feeding unit attached to a feeding port for injecting solvent into the extrusion channel. A solvent feeding unit comprises any device to move/dispense/inject solvent at a controlled rate into the extrusion channel, such as a peristaltic pump, a diaphragm pump, a rotary vane pump, a syringe pump, or any other rotary or positive displacement pump, among others.

Also, in some embodiments at least one input constituent is solid but plasticizes by melting upon heating. In the context of the invention herein a solid constituent that plasticizes by melting upon heating is referred to a solid constituent (e.g., an excipient or an active ingredient) having a viscosity that decreases upon increasing the temperature. Typically, a solid constituent may be considered plasticized as soon as its viscosity has decreased so much that it is of the order of or smaller than the viscosity of a plasticized matrix. Thus, the melting temperature of a solid constituent in the invention herein is referred to the temperature at which the viscosity of said solid constituent has decreased so much upon heating that it is of the order of or smaller than the viscosity of a plasticized matrix. Non-limiting solid constituents that melt upon heating include solid constituents that transition from solid to semi-solid upon heating, solid constituents that transition from solid to liquid upon heating, solid constituents that exhibit a gradual decrease in viscosity upon heating, solid constituents that transition from solid to a plasticized matrix upon heating, and so on. A solid constituent that plasticizes by melting upon heating is preferably chemically stable at elevated temperatures (e.g., at the temperature of a heated housing or a heated fraction thereof).

Thus, for fluidizing (or plasticizing) at least one injected solid constituent, the apparatus herein may further comprise at least one heating element. Said at least one heating element may, for example, be wrapped around the housing or a fraction thereof. In the context of this disclosure, all such heating (or cooling) elements that are partially wrapped around the housing are considered "wrapped around the housing". Non-limiting examples of heating elements that are wrapped around the housing comprise band heaters, coil heaters, etc.

In some embodiments, at least one heating element may be fully or partially embedded into the housing. In the context of this disclosure, all such heating (or cooling) elements that are "fully or partially embedded into the housing" are considered "embedded into the housing". Thus, non-limiting examples of heaters that are embedded into the housing include cartridge heaters fixed in and surrounded by the housing, fluid channels in the housing that are filled with a circulating temperature-controlled fluid, etc. It may be noted that a fluid that circulates through channels of the housing may not only allow to heat the housing or a fraction thereof, but may also allow to cool it. The temperature of the circulating fluid should be lower than the temperature of the housing (or a fraction thereof) in this case. Any more examples of heating elements or examples of how the heating of the housing or an input constituent may be performed would be obvious to a person of ordinary skill in the art. All of them are within the scope of this invention.

In some embodiments of the apparatus or method herein, the housing further comprises at least one sensing port for attaching a sensor to the housing. Said sensor may be selected from the group comprising pressure sensors, temperature sensors, flow rate sensors, sensors for measuring the composition of the material in the extrusion channel (e.g., by near infrared spectroscopy, Fourier transform infrared spectroscopy, nuclear magnetic resonance spectroscopy, raman spectroscopy, etc.), or sensors for determining the physical form of the material in the extrusion channel (e.g., by x-ray spectroscopy, Fourier transform infrared spectroscopy, nuclear magnetic resonance spectroscopy, raman spectroscopy, etc.), and others.

A sensor may, for example, be used to monitor a specific variable or property, or to provide a measured signal for real-time feedback control of a specific variable. Such real-time feedback control is desirable for continuous manufacturing with integrated, real-time quality control. Thus, in some embodiments of the apparatus or method herein, at least one sensor supplies a measured signal to a control loop comprising at least a reference signal (e.g., a target value of the measured signal), an "actuator" (e.g., a motor, heating element, cooling element, valve, etc.), and a sensor.

Figure 14:
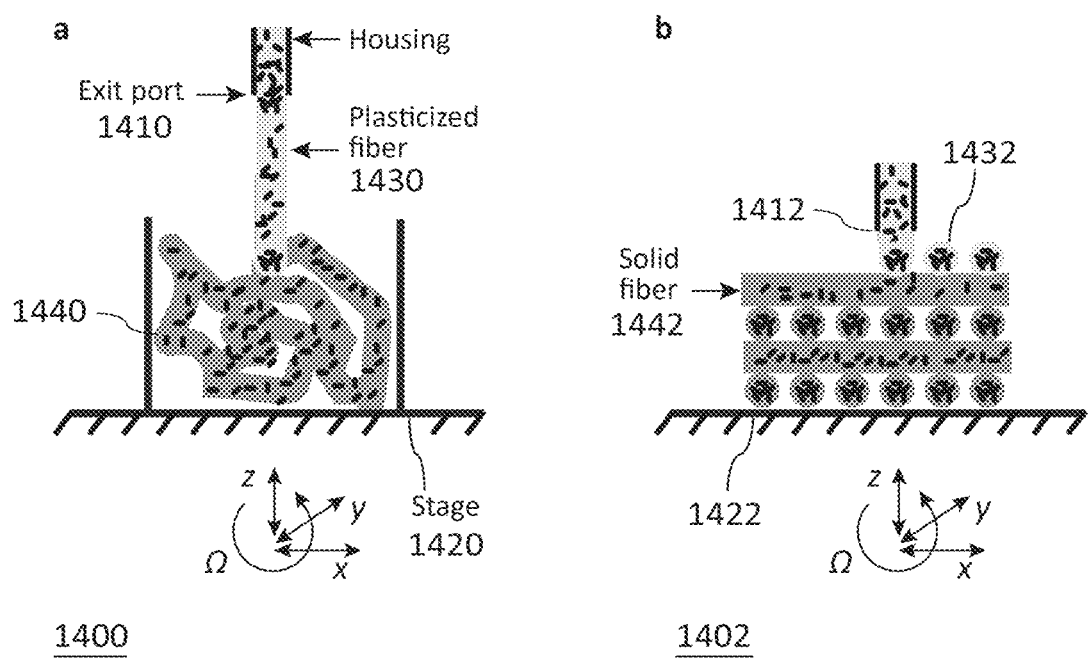
FIG. 14 presents non-limiting schematics of structuring plasticized fibers to fibrous dosage forms according to this invention.

FIG. 14 presents illustrative but not limiting examples 1400, 1402 of an exit port 1410, 1412 and a fiber structuring unit comprising a stage 1420, 1422 to build (e.g., micropattern or 3D-pattern) three dimensional structural networks of fibers. In the context of the invention herein, a stage 1420, 1422 comprises a working platform that does not become part of the dosage form. By way of example but not by way of limitation, said working platform or stage may comprise a solid material, grid, or mold defining a deposition surface on which a plasticized fiber can be patterned. Another non-limiting example of a stage or working platform is a surface or solid framework on which a substrate can be placed (e.g., to which a substrate can be attached). A plasticized fiber may then be deposited or patterned on said substrate.

Thus, in some embodiments of the apparatus herein, the fiber structuring unit comprises a translating or rotating stage for structuring one or more plasticized fibers to a three dimensional structural network of one or more fibers. The term "translating or rotating stage" is understood herein as a stage that can be moved (e.g. a stage that can translate or rotate, or a stage that has the capacity or the ability to translate or rotate) with respect to an exit port. This includes, but is not limited to a stage that can be moved and an exit port that is not movable, or an exit port that is movable and a stage that is not movable, or an exit port that is movable and a stage that is movable.

Similarly, in some embodiments of the method herein, structuring at least one plasticized fiber to a three dimensional structural network of one or more fibers is performed using a translating or rotating stage. Furthermore, in the apparatus or method herein, one or more plasticized fibers may be structured to a three dimensional structural network of fibers by 3D-patterning said one or more plasticized fibers on a substrate defined by or attached to a translating or rotating stage. It may be noted that the terms "stage", "x-y-z stage", "translating or rotating stage", and "translating stage" are used interchangeably in this disclosure.

FIG. 14a shows a non-limiting schematic 1400 of how one or more plasticized fibers 1430 may be structured to a three dimensional structural network of fibers. One or more plasticized fibers 1430 are randomly (or almost randomly) arranged/assembled (or 3D-patterned) on a substrate defined by a stage 1420 or attached to a stage 1420. In the non-limiting example shown the deposition location of a plasticized fiber lies on the deposition surface of the stage 1420 initially, but then after an initial layer of fibers 1440 has been deposited on the stage 1420, the deposition location of a plasticized fiber 1430 lies on the deposited layer of fibers 1440. The plasticized fibers 1430 are arranged randomly (or almost randomly) because the distance between the exit port 1410 and the deposition location 1420, 1440 is so long that the plasticized fiber 1430 can bend before deposition.

FIG. 14b presents another non-limiting schematic 1402 of how one or more plasticized fibers 1432 may be structured to a three dimensional network of one or more fibers. One or more plasticized fibers 1432 are 3D-patterned on a substrate defined by a stage 1422 or attached to a stage 1422. The distance between the exit port 1412 and the deposition location of a plasticized fiber 1432 effluent from said exit port 1412 is small and controlled during 3D-patterning. Thus the one or more plasticized fibers 1432 effluent from the exit port 1412 do not bend randomly (or almost randomly) before deposition. The deposition location of the one or more plasticized fibers 1432 effluent from the exit port 1412 can be precisely controlled as shown. Such precise control of the plasticized fibers' deposition location enables the manufacture of dosage forms with precisely controlled microstructure.

Therefore, for achieving precise control of a plasticized fiber's deposition location, in some embodiments the distance between an exit port and the deposition location of a plasticized fiber effluent from said exit port is no greater than 7 mm during 3D-patterning. This includes, but is not limited to a distance between an exit port and the deposition location of a plasticized fiber effluent from said exit port no greater than 6 mm, or no greater than 5 mm, or no greater than 4 mm, or no greater than 3 mm, or no greater than 2 mm. Furthermore, in some embodiments the distance between an exit port and a deposition location of a plasticized fiber on a substrate is no greater than ten times the thickness of said fiber. This includes, but is not limited to a distance between an exit port and a deposition location of a fiber on a substrate no greater than 9 times, or no greater than 8 times, or no greater than 7 times, or no greater than 6 times, or no greater than 5 times the thickness of said fiber. It may be noted that the deposition location of a plasticized fiber can be the surface of a substrate (e.g., the top surface of an x-y-z stage or the top surface of a deposited fibrous bed or structure, etc.).

Moreover, for achieving precisely controlled fibrous patterns, the velocity of a substrate with respect to an exit port may be of the order of the velocity of a fibrous extrudate effluent from an exit port (e.g., the velocity of a plasticized fiber that exits an exit port or the velocity of a fibrous extrudate). Thus, in some embodiments the velocity of a substrate with respect to an exit port, $v_{st}$, is in the range 0.1-10 times the velocity of a fibrous extrudate, $v_f$. This includes, but is not limited to $v_{st}$ in the range 0.2-5 times $v_f$, or $v_{st}$ in the range 0.3-3 times $v_f$, or $v_{st}$ in the range 0.5-2 times $v_f$. It may be obvious to a person of ordinary skill in the art that the path and velocity of a substrate with respect to an exit port may be computer-controlled.

In addition to the requirements on the kinematics of a substrate with respect to an exit port, a plasticized fiber should be viscous enough to ensure that a precise fibrous pattern is preserved. Thus, in some embodiments the shear viscosity of a plasticized matrix or fiber is greater than 0.1 Pa·s at a shear rate no greater than 10 l/s. This includes, but is not limited to a shear viscosity of a plasticized matrix or fiber greater than 0.5 Pa·s, or greater than 1 Pa·s, or greater than 5 Pa·s, or greater than 10 Pa·s, or greater than 20 Pa·s, or greater than 50 Pa·s, or greater than 100 Pa·s at a shear rate no greater than 10 l/s.

In some embodiments, the viscosity of a plasticized fiber is controlled by the weight fraction of solvent in said fiber. Thus, in some embodiments, the weight fraction of solvent in a plasticized fiber is no greater than 0.925. This includes, but is not limited to a weight fraction of solvent in a plasticized fiber no greater than 0.9, or no greater than 0.85, or no greater than 0.8, or no greater than 0.75, or no greater than 0.7, or no greater than 0.65, or no greater than 0.6.

In some embodiments, an inter-fiber spacing, and/or a fiber thickness, and/or the position of an inter-fiber contact, and/or the contact width of an inter-fiber contact can be precisely (or deterministically) controlled in a fibrous dosage form prepared by the method or apparatus herein. In the context of this invention, a variable (or a parameter, e.g., an inter-fiber spacing or a fiber thickness) is precisely controlled if it is deterministic and not stochastic (or random). A variable or parameter may be deterministic if, upon multiple repetitions of a step that includes said variable, the standard deviation of the values of said variable is smaller than the average value. This includes, but is not limited to a standard deviation of the values of said variable smaller than half the average value, or smaller than one third of the average value, or smaller than a quarter of the average value, or smaller than one fifth or the average value, or smaller than one sixth of the average value of said variable. By way of example but not by way of limitation, if a fiber is produced multiple times under identical conditions, the standard deviation of the thickness of said fibers is less than the average value of said fibers' thickness. Similarly, if an inter-fiber spacing is produced multiple times under identical conditions, the standard deviation of said inter-fiber spacing is less than the average value of said inter-fiber spacing in some embodiments of the invention herein.

After patterning on a substrate, a plasticized fiber may be solidified. In the invention herein, solidification of a plasticized fiber is referred to as increasing the viscosity of said plasticized fiber by at least two times. This includes, but is not limited to increasing the viscosity of said plasticized fiber by at least three times, or by at least four times, or by at least five times, or by at least six times, or by at least seven times, or by at least ten times, or by at least 20 times. In the extreme case, the viscosity of a solidified fiber is very large and may be considered "infinite". In this extreme case, the solidified fiber can be considered an "elastic" material.

A plasticized fiber may be solidified by various ways. By way of example but not by way of limitation, depending on the composition of said plasticized fiber, solidification may be by evaporating solvent, or by cooling (e.g., by cooling the plasticized fiber to below its melting temperature), or by cross-linking some of the constituents.

To accelerate or control the rate at which solvent is evaporated, the apparatus herein may further comprise a unit for evaporating solvent from the three dimensional network of fibers. Such units for evaporating solvent include, but are not limited to, devices for blowing a warm gas (e.g., air, nitrogen, argon, $CO_2$, etc.) on and/or through the three dimensional structural network of fibers, drying ovens with temperature and pressure control, temperature-controlled stages or substrates, and so on. Similarly, to accelerate or control the rate at which a fiber is cooled, the apparatus herein may further comprise a unit for cooling the three dimensional structural network of fibers. Such units include, but are not limited to temperature-controlled stages or substrates (e.g., low-temperature stages or substrates), devices for blowing cool air or gas on and/or through the fibrous structure, and so on.

Furthermore, for accelerating or controlling the rate at which solvent is removed from the fibrous structure, or for accelerating or controlling the cooling rate, in some embodiments the stage or substrate on which the three dimensional structural network of fibers is deposited may comprise at least a perforation (e.g., one or more perforations, at least a hole, one or more holes, at least a pore, one or more pores, a grid, etc.) that is impermeable to a deposited fiber but permits gas flow through it.

Figure 15:
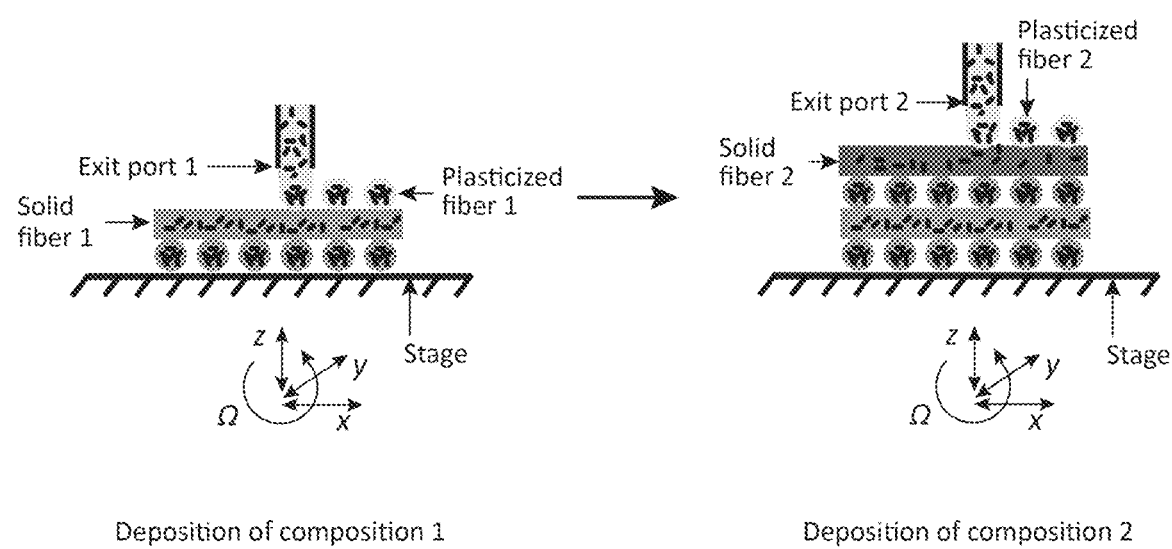
FIG. 15 shows a non-limiting schematic of structuring multiple fibers of multiple compositions to a fibrous dosage form structure according to this invention.

As shown in the illustrative but not limiting example of FIG. 15, any apparatus or method disclosed herein may be adapted to manufacture fibrous dosage forms comprising multiple fibers of different compositions. By way of example but not by way of limitation, plasticized fiber 1 with composition 1 may first be extruded through exit port 1 and the plasticized fiber 1 deposited on a substrate. Then plasticized matrix 2 with composition 2 may be extruded through exit port 2 and the plasticized fiber 2 deposited on a substrate. Furthermore, an exit port through which a plasticized matrix is extruded may be surrounded by another exit port through which another plasticized matrix is extruded. Fibers with heterogeneous composition of the cross section may be produced that way.

The fibrous dosage forms produced by some embodiments of the apparatus or method herein disintegrate in a time no greater than about 60 minutes after immersion in a dissolution fluid. This includes, but is not limited to a disintegration time no greater than 50 minutes, or no greater than 40 minutes, or no greater than 30 minutes, or no greater than 25 minutes, or no greater than 20 minutes, or no greater than 15 minutes, or no greater than 10 minutes after immersion in a dissolution fluid.

Furthermore, in some embodiments the one or more fibers have an average thickness ho no greater than 2.5 mm. This includes, but is not limited to ho no greater than 2 mm, or no greater than 1.5 mm, or in the ranges of 0.1 µm to 2.5 mm, 0.5 µm to 2.5 mm, 1 µm to 2.5 mm, 1.75 µm to 2.5 mm, 2.5 µm to 2.5 mm, 2.5 µm-2 mm, 5 µm-2.5 mm, 10 µm-2.5 mm, 15 µm-2.5 mm, 20 µm-2.5 mm, 30 µm-2.5 mm, 40 µm-2.5 mm, or 50 µm-2.5 mm.

In some embodiments, the contact width between fibers (or fiber segments) on average is no greater than 2.5 mm. This includes, but is not limited to a contact width between fibers no greater than 2 mm, or no greater than 1.75 mm, or no greater than 1.5 mm. In other examples without limitation, a contact width, 2a, between fibers may be no greater than 1.1 times the thickness of the contacting fibers (or fiber segments) at the position of the contact.

Moreover, in some embodiments the effective free spacing, $A_f e$, on average is greater than 0.1 µm. This includes, but is not limited to an average $A_f e$ greater than 0.25 µm, or greater than 0.5 µm, or greater than 1 µm, or greater than 2 µm, or greater than 5 µm, or greater than 7 µm, or greater than 10 µm, or greater than 15 µm, or greater than 20 µm, or greater than 25 µm, or greater than 30 µm, or greater than 40 µm, or greater than 50 µm, or in the ranges of 0.1 µm-5 mm, 0.1 µm-3 mm, 0.25 µm-5 mm, 0.5 µm-5 mm, 0.25 µm-3 mm, 0.1 µm-2.5 mm, 1 µm-2.5 mm, 5 µm-2.5 mm, 10 µm-2.5 mm, 15 µm-3 mm, 20 µm-3 mm, 30 µm-3 mm, 40 µm-3 mm, or 50 µm-3 mm. The "effective free spacing" between adjoining fiber segments is defined as the maximum diameter of a sphere that fits in the corresponding free space considering the fibers as rigid, fixed bodies. The diameter of such spheres may be estimated from 2-d images of the microstructure. Such 2-d images may be obtained from scanning electron micrographs of the cross section of the dosage form. The greatest circles that fit in the free spaces of the microstructure may be drawn on the scanning electron micrograph (e.g., the 2-d image) and the average diameter of the circles (e.g., the average effective free spacing) calculated. It may be noted that in the context of the invention herein, the average effective free spacing (e.g., the effective free spacing on average) is referred to a volume-average, or area-average, or line-average effective free spacing rather than a number-average effective free spacing. The above constraints on the effective free spacing are primarily for ensuring that dissolution fluid can percolate into and flow through the fibrous structure at moderate velocity. This enables that the disintegration time of the "thick" dosage form is of the order of the disintegration time of a "thin" single fiber.

Further details related to the disintegration of and drug release by fibrous dosage forms, and the definitions of ho, a, and $A_f e$ can be found in the U.S. patent application Ser. No. 15/482,776.

FURTHER EXPERIMENTAL AND THEORETICAL EXAMPLES

The following non-limiting examples set forth, in detail, ways by which the fibrous dosage forms may be prepared and analyzed, and will enable one of skill in the art to more readily understand the principle thereof. The following examples are presented by way of illustration and are not meant to be limiting in any way.

Figure 16:
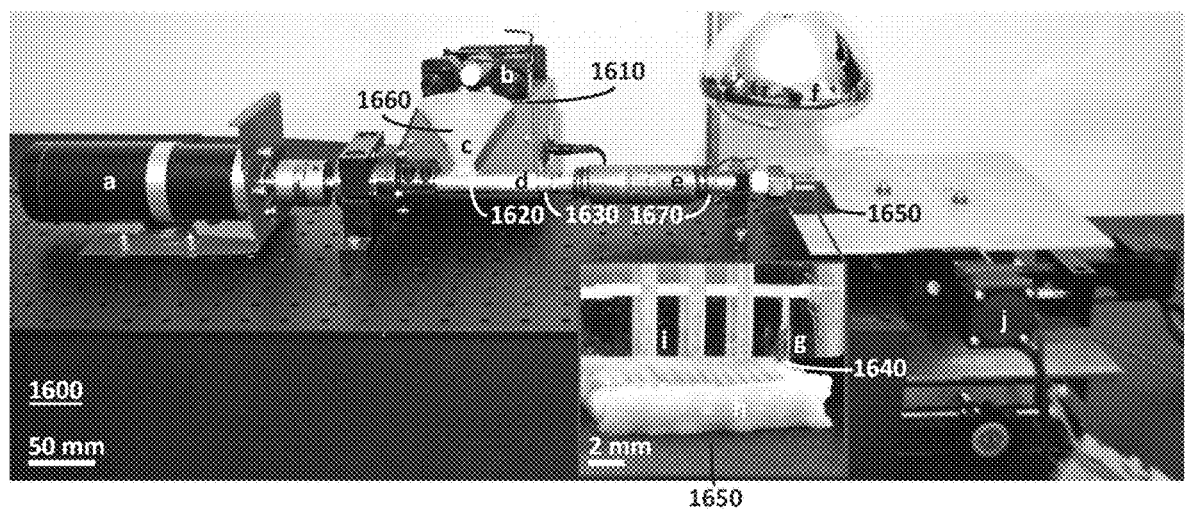
FIG. 16 is a photograph of the apparatus to manufacture the non-limiting experimental examples of melt-processed fibrous dosage forms disclosed herein. The apparatus comprises the components: (a) motor, (b) syringe pump, (c) hopper, (d) extrusion screw and barrel (e.g., housing, extrusion channel, and conveying element), (e) heater, (f) infrared lamp (e.g., heater), (g) extruder nozzle exit (e.g., exit port), (h) deposited fiber bed, (i) supply channels for cooling fluid, and (j) x-y-z stage.

Example 1: Apparatus for Preparing Melt-Processed Single Fibers and Dosage Forms FIG. 16 is a photograph of an apparatus 1600 to prepare melt-processed fibrous dosage forms. It includes the following elements or units: a granular solid feeding unit 1610, a housing 1630 defining an extrusion channel, an extrusion screw 1620 (i.e., the screw 1620 is inside the housing 1630), a wrap around 1670 and an infrared heater, an exit port 1640 of the extrusion channel where the fibrous melt exits, and an x-y-z stage 1650 for building the fibrous structure.

The granular solid feeding unit 1610 consists of a syringe with uniform barrel diameter and a syringe pump to inject one or more granular solids into a hopper 1660. The volumetric flow rate is controlled by velocity control of the syringe's piston. The hopper 1660 directs the granules into the extrusion channel through a granular solids feeding port in the housing. The material (e.g., the one or more granular solids) in the extrusion channel is conveyed forward by the rotating extrusion screw 1620. The extrusion screw 1620 is 244 mm long, has an outer diameter of 10 mm, a helix angle of 17.65°, a screw channel height of 1 mm, and a screw channel width of 8.5 mm. The housing is surrounded by a resistance heater coil (i.e., the wrap around heater) 1670 to set the temperature of the housing 1630 and extrusion channel (e.g., to plasticize the injected one or more granular solids by melting). The radius of the extrusion channel is uniform and equal to 5 mm at the location of the screw, but it tapers down before the exit port to the radius of said exit port. The radius of the exit port (e.g., the nominal radius of a plasticized fiber, $R_n$, extruded through the exit port) is 0.25 mm. The x-y-z stage 1650 is positioned right underneath the exit port.

Example 2: Apparatus for Preparing Wet-Processed Single Fibers and Dosage Forms The apparatus presented in the non-limiting experimental example 1 above may adapted for preparing wet-processed single fibers and dosage forms. Specifically, in the non-limiting experimental examples herein, a second feeding port for injecting at least one solvent into the extrusion channel is added to the housing between the granular solids feeding port and the exit port. Also, a solvent feeding unit attached to the second feeding port is added. The solvent feeding unit consists of a syringe with uniform barrel diameter and a syringe pump to control the volumetric flow rate at which solvent is injected into the extrusion channel. Additionally, a temperature-controlled fan is added to blow warm air on the plasticized micro-patterned fibers for accelerating solvent removal from the fibrous structure.

Example 3: Preparation of Melt-Processed Single Fibers and Dosage Forms

Melt-processed single fibers, fibrous dosage forms, and minimally-porous (or non-porous) dosage forms were prepared by first mixing 40 wt % of solid acetaminophen particles with 60 wt % polyethylene glycol 35,000 (PEG 35k) granules. The solid mixture was then loaded into the granular solid feeding unit set to deliver 1.7 mg/s. The rotation rate of the screw was about 3-5 rpm and the temperature of the housing was set to 80° C.

For preparing melt-processed single fibers and fibrous dosage forms, the fibrous extrudate was deposited along the desired path on the x-y-z stage. The ambient and stage temperatures were 25° C. during deposition, thus the deposited fiber bed cooled and solidified soon after it was formed. A photograph of a fiber bed during fiber deposition (or 3D-micro-patterning) is shown in the magnified window of FIG. 16. Six different structures were prepared: single fibers with nominal radius, $R_n$=250, 500, and 1000 μm (as given by the radius of the exit port), and three dimensional structural networks of one or more fibers (e.g., fibrous dosage forms) of the configuration shown in FIG. 1b with $R_n$=250 μm and nominal inter-fiber spacing, =1750, 900, and 600 μm (as determined by the path of the x-y-z stage). The velocity of the stage was 7.3 mm/s while the fiber and fibrous forms with $R_n$=250 μm were deposited, and 1.8 and 0.45 mm/s, respectively, for depositing the fibers with $R_n$=500 and 1000 μm. Also, during deposition the distance between the exit port and the top of the stage or fibrous bed was kept at about 1-3 mm. The process was stopped when the single fiber was deposited, or, in case of fibrous dosage forms, the thickness of the fibrous bed (i.e., the 3D-micro-patterned structure or the three dimensional network of one or more fibers) reached about 5 mm. The melt-processed fibrous dosage forms prepared were square disks: 10 mm in side length and about 5 mm in thickness.

For preparing melt-processed minimally-porous solid dosage forms, a stainless steel mold was placed on (e.g., attached to) the x-y-z stage and was filled with the plasticized fibrous stream effluent the exit port until a height of about 5 mm was reached. The temperature of the mold was 25° C. The material was left in the mold for about 2 minutes to solidify and the solid dosage form was subsequently ejected. The melt-processed non-porous dosage forms prepared were circular disks: 13 mm in diameter and 5 mm in thickness.

Example 4: Preparation of Wet-Processed Single Fibers and Dosage Forms

In the wet-processed single fibers and fibrous and minimally-porous dosage forms, the drug was ibuprofen which was received as solid particles from BASF, Ludwigshafen, Germany. The excipient was a polyvinyl alcohol-polyethylene glycol graft copolymer 3:1 of molecular weight 45 kg/mol (tradename: Kollicoat IR; BASF, Ludwigshafen, Germany). The solvent was deionized water.

The single fibers, and fibrous and minimally-porous dosage forms were prepared by first mixing 60 wt % of solid ibuprofen particles with 40 wt % particles of the excipient. The solid mixture was then loaded into the granular solids feeding unit set to deliver 1.7 mg/s. The solvent-feeding unit delivered 1.13 mm$^3$/s of deionized water. The rotation rate of the extrusion screw was 3-5 rpm.

For preparing the single fibers and fibrous dosage forms, the fibrous extrudate was deposited along the desired path on the x-y-z stage. Two different structures were prepared: single fibers with nominal radius, $R_n$=250 μm (the internal radius of the exit port), and fibrous dosage forms of the configuration shown in FIG. 9 with $R_n$=250 μm $R_p$ and nominal inter-fiber spacing, $\lambda_n$=900 μm≈$\lambda_p$. The velocity of the stage was 14.4 mm/s during deposition. The distance between the exit port and the top plane of the substrate (e.g., the top surface of the linear stage or fiber bed) was kept at 1 to 2 mm. The process was stopped when a single fiber was deposited or, in the case of a fibrous dosage form, 10 fibrous layers were patterned. During and after patterning, the fiber and the fibrous structure (e.g., the three dimensional network of or one or more fibers) were dried by blowing warm air at 60° C. for 4 minutes. The wet-processed fibrous dosage forms were square disks of 10 mm on the side and about 4 mm in thickness.

Figure 17:
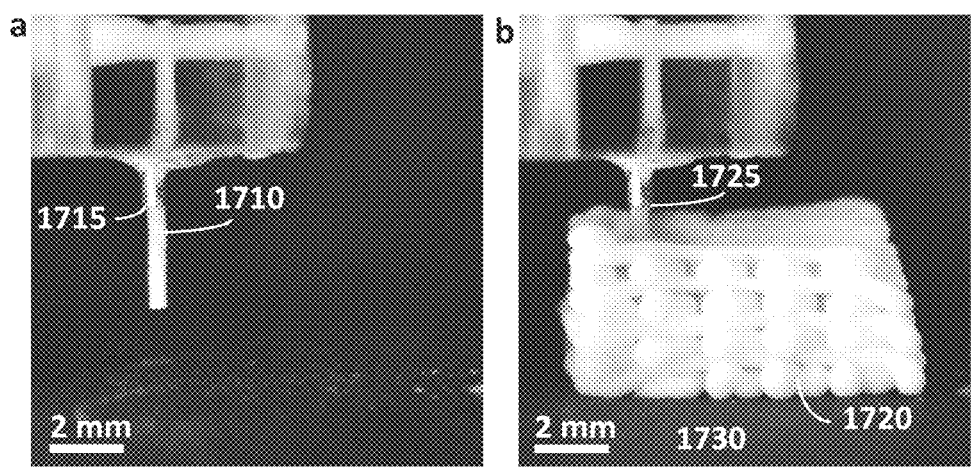
FIG. 17 presents photographs of the manufacture of fibrous dosage forms: (a) single fiber exiting the extrusion channel, and (b) manufacture of a fibrous dosage form by patterning the fibrous extrudate along the desired path.

FIG. 17 shows a wet-processed single fiber 1710 exiting an exit port 1715 (e.g., a wet fibrous extrudate or fibrous extrudate). Also shown is an exit port 1725 and stage 1730 while building a wet-processed fibrous dosage form 1720 (e.g., while structuring at least one plasticized fiber to a three dimensional network of one or more fibers).

To prepare the minimally-porous solid dosage forms, a stainless steel mold was placed on the linear stage and was filled with the extrudate until the plasticized material reached a height of about 5 mm. The dosage form in the mold was then allowed to dry for 48 hours in a dry environment at 25° C. The minimally-porous dosage forms were circular disks: 13 mm in diameter and about 4 mm in thickness.

Example 5: Drying of Wet-Processed Single Fibers

For determining the drying time of the fibers, a single fiber was prepared as above and was deposited in a weighing boat. The boat containing single fiber was then exposed to a stream of air at a temperature of 60° C. and a velocity of 2.3 m/s. The weight of the fiber was measured at the times 0, 50, 100, 150, 200, and 300 seconds after exposure to the air stream. The fraction of residual solvent as a function of time, $M(t)/M_0$, was calculated as:

$$\frac{M(t)}{M_0} = \frac{w(t) - w_\infty}{w_0 - w_\infty} \quad (26)$$

where w(t) is the weight of the fiber at time t, $w_0$ the initial weight of the wet fiber, and $w_\infty$ the weight of the dry fiber.

Figure 18:
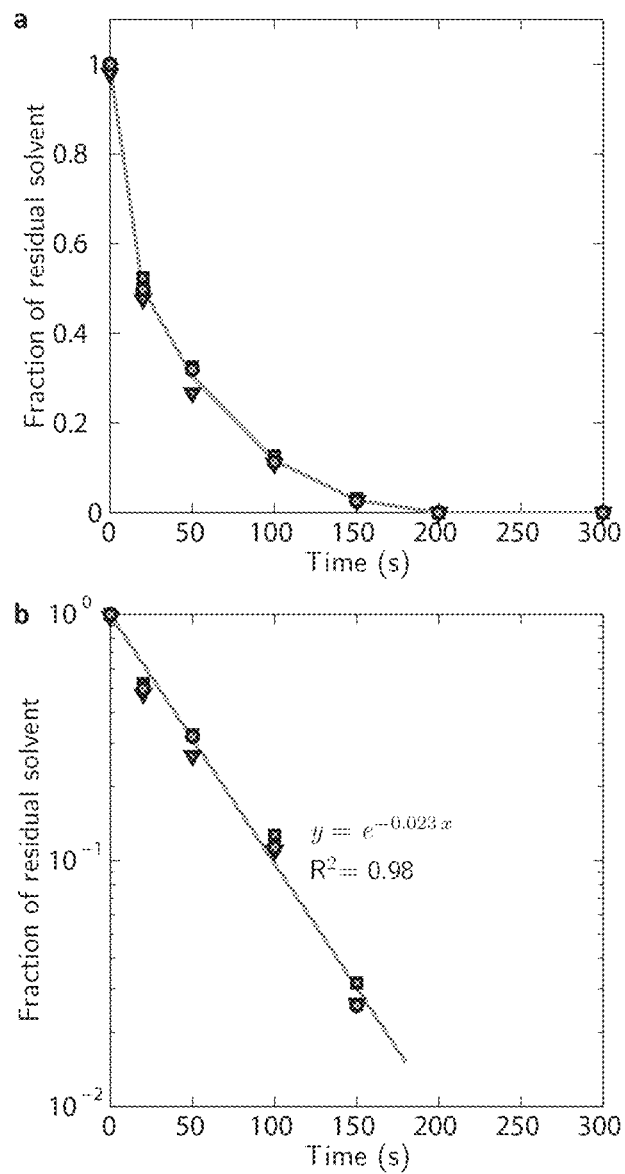
FIG. 18 presents data of the rate at which solvent is removed from wet fibers.

The fraction of residual solvent in the wet fibers versus time after exposure to the air stream (T=60° C., $v_{g,\infty}$=2.3 m/s) is shown in FIG. 18a. $M(t)/M_0$ decreased rapidly with time and then approached the final value 0.

FIG. 18b is a semi-log plot of the fraction of residual solvent versus time. The data could be fitted to the curve $M(t)/M_0$=exp(−0.023t). Thus the decay was exponential and the drying time constant, $\tau_d$=1/0.023=43.48 s. From Eq. (19), $\tau_d \approx \beta_1^2 D_{solv}/R_p^2$, where $\beta_1$ is the dominant root of Eq. (17). Using $R_p$=250 µm and $\beta_1$=2.4 the diffusion coefficient of the solvent in the wet fiber, $D_{solv} \approx R_p^2/\tau_d \beta_1^2 = 2.5 \times 10^{-10}$ m²/s.

Example 6: Microstructures of Single Fibers and Dosage Forms

The microstructures of the fibers and dosage forms were imaged using a Zeiss Merlin High Resolution SEM with a Gemini column. Top view images were obtained without any preparation of the sample. For imaging the front views, however, the structures were cut with a thin blade (MX Ultra; Thermo Scientific, Waltham, Mass.) prior to imaging. Imaging was done with an in-lens secondary electron detector. The accelerating voltage to operate the microscope was 5 kV and the probe current was 95 pA.

Figure 19:
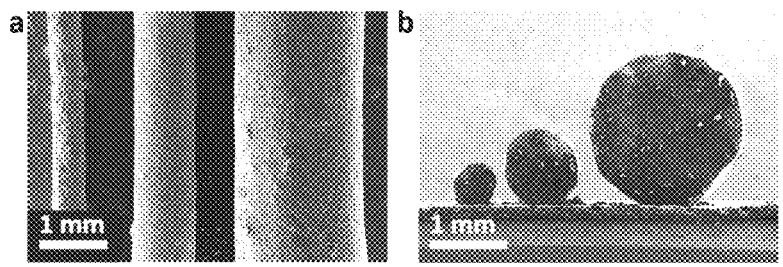
FIG. 19 shows scanning electron micrographs of the microstructures of melt-processed single fibers.

FIG. 19 presents representative SEM images of the melt-processed single fibers with drug particles embedded in an excipient matrix. The longitudinal views are given in FIG. 19a and the FIG. 19b shows the cross sections. The radii of the fibers are about 240, 456, and 954 µm, respectively, roughly the same as the inner diameter of the respective exit ports (Table 1).

Figure 20:
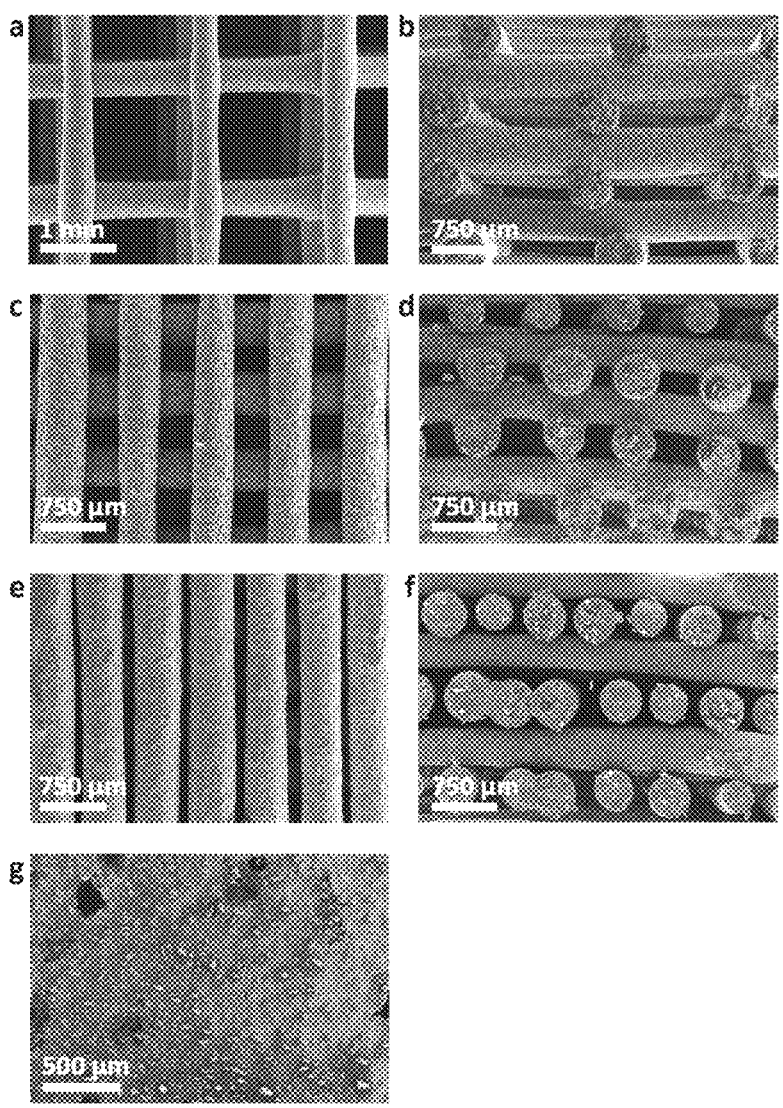
FIG. 20 depicts scanning electron micrographs of the microstructures of melt-processed dosage forms according to this invention.

Scanning electron micrographs of the structures of melt-processed dosage forms are shown in FIG. 20. FIGS. 20a-f are microstructures of the fibrous dosage forms (e.g., three dimensional structural networks of one or more fibers). The initial fiber radius, $R_0$, and inter-fiber distance, $\lambda_0$, are predictable and agree well with the nominal parameters set by the x-y-z stage as summarized in Table 1. FIG. 20g is the microstructure of an essentially non-porous solid dosage form with drug particles embedded in an excipient matrix.

Figure 21:
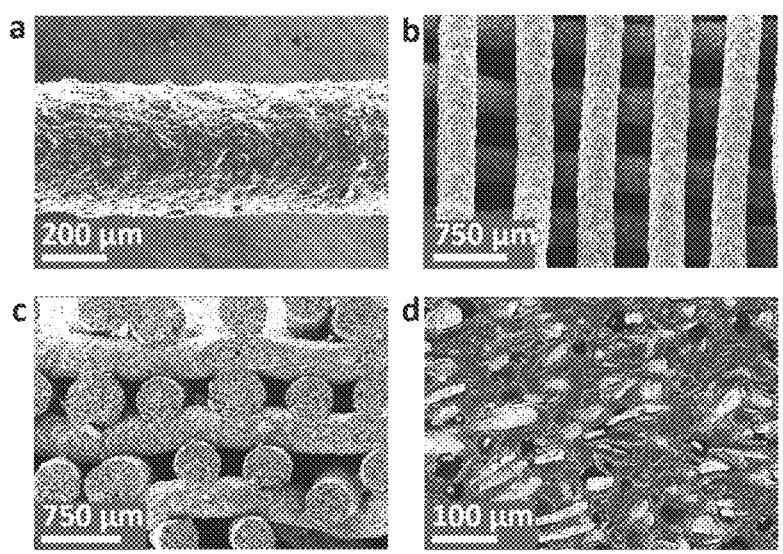
FIG. 21 depicts scanning electron micrographs of the microstructures of wet-processed single fibers and dosage forms according to this invention.

Scanning electron micrographs of the wet-processed single fiber and dosage forms are shown in FIG. 21. FIG. 21a is the longitudinal view of the single fiber. The fiber diameter was roughly 408 µm, slightly smaller than the inner diameter of the exit port. FIGS. 21b and 21c, respectively, are the top and front views of the fibrous dosage form (e.g., the three dimensional structural network of one or more fibers). The radius of the solid fibers, $R_s$, and the interfiber distance, $\lambda_s$, were predictable by Eq. (25), as shown in Table 2. The radius of the crossed fibers' contact was 172.3±23.4 µm, about the same as the value calculated by Eq. (11). Finally, FIG. 21d presents the microstructure of a minimally-porous solid dosage form (the same as the microstructure of a single fiber). Drug particles are embedded in the excipient matrix.

Example 7: Drug Release by Melt-Processed Single Fibers and Dosage Forms

Drug release by the melt-processed single fibers and dosage forms was tested with a USP apparatus 1 (as shown in The United States Pharmacopeial Convention, USP 39-NF 34). The dosage forms were put in the dissolution basket inside a vessel filled with 900 ml of the dissolution fluid (a 0.05 M phosphate buffer solution prepared with sodium phosphate monobasic and sodium phosphate dibasic at a pH of 5.8 and at 37° C.). The basket was then rotated at 50 rpm. The concentration of dissolved drug was measured versus time by UV absorption at 240 nm using a fiber optic probe (Pion, Inc.).

Figure 22:
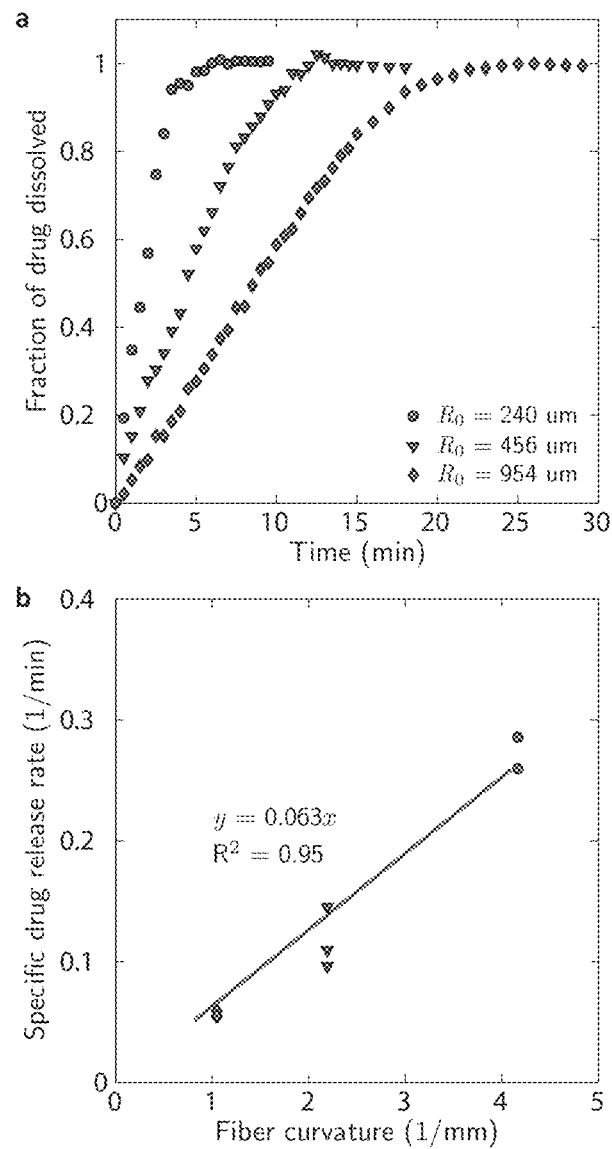
FIG. 22 presents the results of the fraction of drug dissolved versus time of melt-processed single fibers.

FIG. 22a presents representative curves of the fraction of drug dissolved versus time by the melt-processed single fibers. For all the fibers, the fraction of drug dissolved increased steadily until it plateaued out to the final value. The times to dissolve 80% of the drug content, $t_{0.8}$, of the fibers tested are listed in Table 1. $t_{0.8}$ increased as the initial fiber radius was increased, from about 2.9 minutes if $R_0$=240 µm to 14.25 minutes if $R_0$=954 µm. The drug release rate was limited by the rate at which the fibers eroded (e.g., by the erosion rate or disintegration rate of the fibers).

The approximate initial drug release flux from the fibers, $$j_{d,0} \cong \frac{0.8 M_{d,0}}{t_{0.8}} \frac{1}{A_0} = \frac{0.8}{t_{0.8}} \frac{f_d \rho_s R_0}{2} \quad (27)$$

is tabulated in Table 1 ($0.8 M_{d,0}/t_{0.8}$ is the time-average drug release rate, $A_0$ the initial fiber surface area, $f_d$ the drug weight fraction in the fiber, and $\rho_s$ the density of the solid fiber). $j_{d,0}$ was between 0.21 and 0.26 µg/mm²s, roughly the same for all the fibers (Table 1). The dependence of the drug release flux on fiber radius was thus small.

The specific drug release rate (i.e., the time-average drug release rate divided by the initial drug content, $0.8/t_{0.8}$) is plotted versus the fiber curvature (i.e., the inverse of the initial fiber radius, $1/R_0$) in FIG. 22b. $0.8/t_{0.8}$ was roughly proportional to $1/R_0$ and could be fitted to the curve $0.8/t_{0.8}$=0.063/$R_0$. Thus because the initial specific surface area of a fiber, $A_{s,0}$=2/$R_0$, the specific drug release rate was directly proportional to $A_{s,0}$, $0.8/t_{0.8}$=0.033×$A_{s,0}$.

Figure 23:
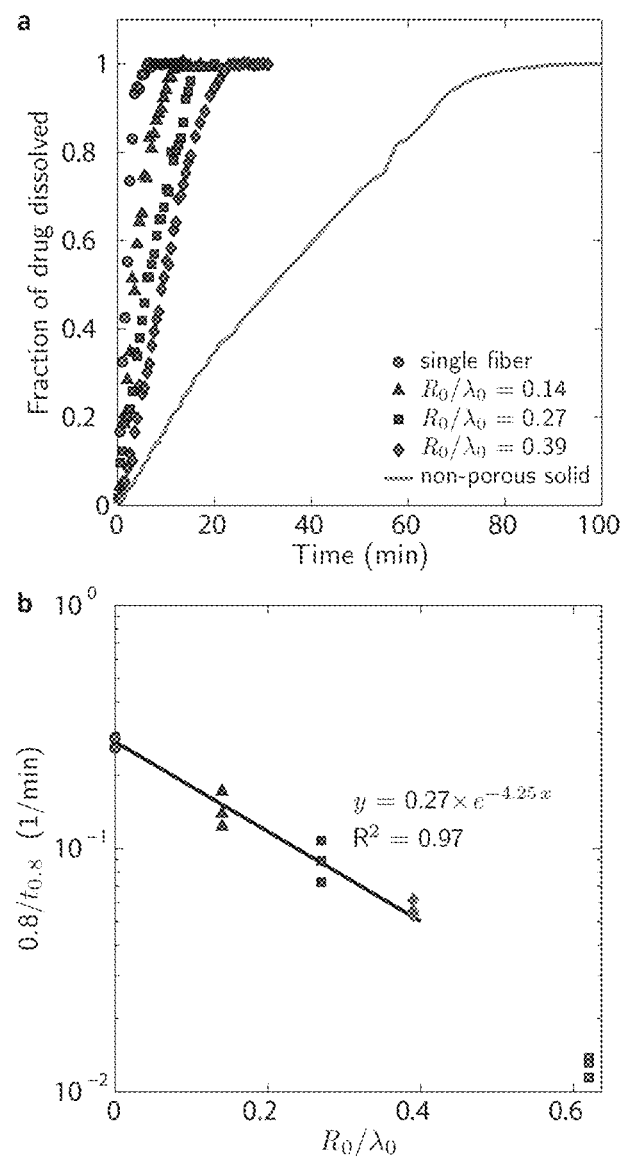
FIG. 23 displays the results of the fraction of drug dissolved versus time of melt-processed dosage forms according to this invention.

FIG. 23a shows representative curves of the fraction of drug dissolved versus time by the fibrous dosage forms together with the results of a single fiber and the non-porous solid structure. $t_{0.8}$ of the fibrous dosage forms was between 5.64 ($R_0/\lambda_0$=0.14) and 14.2 mins ($R_0/\lambda_0$=0.39), much faster than the average value of the non-porous solid dosage forms, $t_{0.8}$=63 mins.

FIG. 23b presents the specific drug release rates of the dosage forms versus $R_0/\lambda_0$. The data of the fibrous forms could be fitted to an exponential curve. The specific release rates of the non-porous solid forms, however, did not follow this curve and were substantially smaller than "predicted" by the fit equation.

Example 8: Drug Release by Wet-Processed Single Fibers and Dosage Forms

Drug release by the wet-processed single fibers and dosage forms was tested with a USP apparatus 1 (as shown in The United States Pharmacopeial Convention, USP 39-NF 34), too. The dosage forms were put in the dissolution basket inside a vessel filled with 900 ml of the dissolution fluid (here a 0.05 M phosphate buffer solution prepared with sodium phosphate monobasic and sodium phosphate dibasic at a pH of 7.2 and at 37° C.). The basket was rotated at 50 rpm during the experiments. The concentration of dissolved drug was measured versus time by UV absorption at 220 nm using a fiber optic probe (Pion, Inc.).

Figure 24:
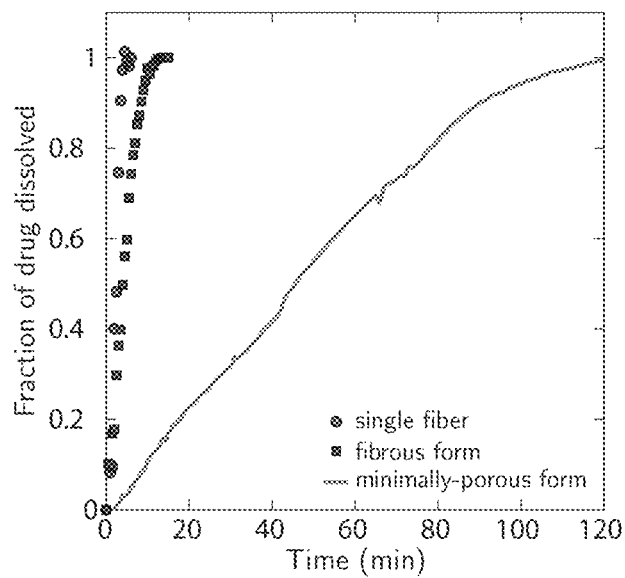
FIG. 24 shows the results of the fraction of drug dissolved versus time of wet-processed single fibers and dosage forms according to this invention.

FIG. 24 shows representative curves of the fraction of drug dissolved versus time of the wet-processed fibrous dosage form together with the data of a wet-processed single fiber and the drug release results of the wet-processed minimally-porous dosage form. For all cases, the fraction of drug dissolved increased steadily with time until it plateaued out to the final value.

The times to dissolve 80% of the drug content, $t_{0.8}$, were extracted from these curves. The $t_{0.8}$ values of the fibers and dosage forms are listed in Table 2. The average $t_{0.8}$ of the single fibers was roughly 3.5 min, and that of the fibrous dosage forms 7.8 min. The average $t_{0.8}$ of the fibrous forms was much smaller than that of the corresponding minimally-porous solid forms, which was 79.3 min.

TABLE 1

Summary of microstructural parameters and drug dissolution times of melt-processed single fibers, melt-processed fibrous dosage forms, and melt-processed minimally-porous solid dosage forms.

| | $R_0$ (μm) | $\lambda_0$ (μm) | $R_0/\lambda_0$ | $\varphi_s$ | $t_{0.8}$ (min) | $j_{d,0}$ (μg/mm²s) |
|---|---|---|---|---|---|---|
| Single fibers | | | | | | |
| A | 240 ± 6 | — | — | 0.0+ | 2.89 | 0.26 |
| B | 456 ± 13 | — | — | 0.0+ | 7.03 | 0.21 |
| C | 954 ± 16 | — | — | 0.0+ | 14.25 | 0.21 |
| Fibrous dosage forms | | | | | | |
| D | 245 ± 28 | 1783 ± 47 | 0.14 | 0.22 | 5.64 | — |
| E | 253 ± 17 | 922 ± 38 | 0.27 | 0.43 | 9.14 | — |
| F | 243 ± 13 | 629 ± 70 | 0.39 | 0.61 | 14.17 | — |
| Minimally-porous solid form | | | | | | |
| G | — | — | — | 0.98 | 63.00 | 0.25 |

The nominal fiber radii, $R_n$, were 250 μm (A, D, E, and F), 500 μm (B), and 1000 μm (C). The nominal initial inter-fiber distances, $\lambda_n$, were 1750 μm (D), 900 μm (E), and 600 μm (F).
The initial fiber radius, $R_0$, and fiber-to-fiber distance, $\lambda_0$, were obtained from the SEM images shown in FIGS. 19 and 20.
$t_{0.8}$ is the time to dissolve 80% of the drug contained in the dosage form. It was derived from the results of drug release experiments shown in FIGS. 22 and 23.
The initial drug release flux, $j_{d,0}$, of the single fibers was derived from Eq. (27) using $f_d$ = 0.4, $t_{0.8}$ as tabulated above, $\rho_s = f_d \times \rho_d + (1 - f_d) \times \rho_e$, $\rho_d$ = 1260 kg/m³, and $\rho_e$ = 1150 kg/m³. The equation used to calculate the initial drug release flux from the faces of the minimally-porous solid dosage forms is: $j_{d,0} = 0.8H_0\rho_s f_d/2t_{0.8}$.

TABLE 2

Summary of microstructural parameters and drug dissolution times of single solid fibers, fibrous solid dosage forms, and minimally-porous solid dosage forms. The nominal fiber diameter, $2R_n$ = 500 μm and the nominal inter-fiber distance, $\lambda_n$ = 900 μm.

| | $2R_s$ (μm) | $\lambda_s$ (μm) | $2a_s$ (μm) | $R_s/\lambda_s$ | $\varphi_s$ | $t_{0.8}$ (min) |
|---|---|---|---|---|---|---|
| A | 408 ± 11 | — | — | — | — | 3, 3.5, 4 |
| B | 404 ± 68 | 745 ± 76 | 345 ± 47 | 0.27 | 0.43 | 7, 7, 5, 9 |
| C | — | — | — | — | — | 77, 79, 82 |

A: single fiber;
B: fibrous dosage form;
C: minimally-porous dosage form
$R_s$, $\lambda_s$, and $a_s$ are obtained from the SEM images of FIG. 21.
Volume fraction of solid fibers in the fibrous dosage form, $\varphi_s \approx \pi R_s/2\lambda_s$.
Calculated values of $R_s$ and $\lambda_s$ are $R_s$ = 210 μm and $\lambda_s$ = 756 μm (by replacing $R_p$ and $\lambda_p$ with $R_n$ and $\lambda_n$ in Eq. (25)).

Example 9: Viscosity of Wet Plasticized Material

The shear viscosity of the plasticized material (a drug-excipient-water suspension consisting of 36 wt % ibuprofen particles, 24 wt % Kollicoat IR, and 40 wt % water) was determined by shear rheometry. The shear rheometer (ARG2 Rheometer, stress-controlled; TA Instruments) was equipped with a 60 mm diameter cone with an apex angle of 178°. The temperature was 37° C. during the experiments, and the shear strain-rate range was 0.01-100 1/s.

FIG. 25 presents the results of the shear viscosity versus shear strain rate of the drug-excipient-water suspension (36 wt % drug, 24 wt % excipient, and 40 wt % water). The shear viscosity of this formulation could be fitted to the curve $\mu_s = 321 \times \dot{\gamma}_s^{-0.65}$. Thus by combining this result with Eq. (4), m=321 Pa·s$^n$ and n=0.35.

The shear viscosity of water-penetrated excipient solutions (mixtures of water and Kollicoat IR at polymer concentrations of 2.5 to 40 wt %) was measured with the same apparatus as above. The temperature during the experiments was again 37° C. The shear strain-rate range, however, was 1-100 1/s.

Figure 26:
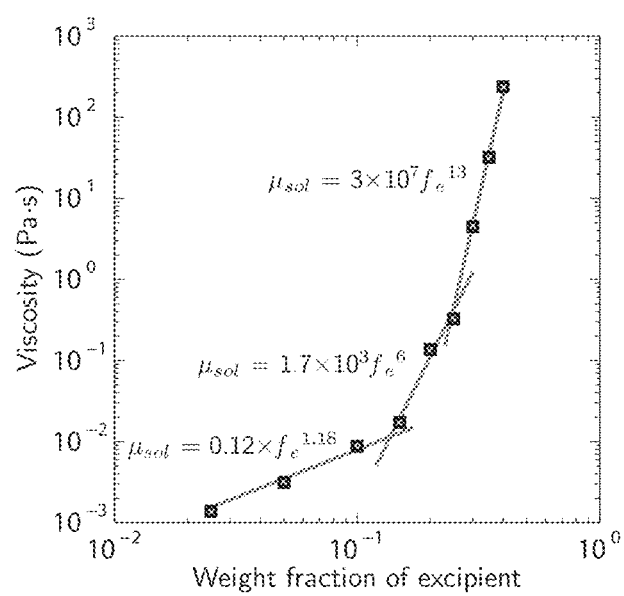
FIG. 26 shows the results of shear viscosity measurements of additional water-excipient solutions versus weight fraction of the polymeric excipient. Polyvinyl alcohol-polyethylene glycol graft copolymer 3:1 with a molecular weight of 45,000 Daltons (tradename: Kollicoat IR) was the excipient.

FIG. 26 presents the shear viscosity of excipient-water solutions (without drug particles) versus weight fraction of excipient, $f_e$, at the shear rate 1 1/s ($f_e$=1−$f_w$, the weight fraction of water). At small weight fractions of the excipient (i.e. in the range 0.025≤$f_e$≤0.14), the shear viscosity roughly followed $\mu_{sol}$=0.12×$f_e^{1.18}$. Then if 0.14<$f_e$≤0.25, the shear viscosity was about $\mu_{sol}$=1.7×10³$f_e^6$, a much stronger dependence on $f_e$. In the range 0.25<$f_e$≤0.4, the dependence on $f_e$ was even stronger: the viscosity roughly followed $\mu_{sol}$=3×10⁷$f_e^{13}$. These results suggest that the viscosity was probably an exponential function of the weight fraction of excipient, linearized piece-wise here.

The solution may be considered dilute up to $f_e$≈0.14, semi-dilute if 0.14<$f_e$≤0.25, and concentrated if $f_e$ is greater than about 0.25. The excipient disentanglement concentration, $c_e^* \approx 140$ kg/m³ (0.14).

Example 10: Reynolds and Capillary Numbers at the Exit Port

The Reynolds number based on the average velocity of flow through a converging channel (e.g., an extrusion channel that tapers down before an exit port) is typically greatest at the exit where the diameter is the smallest. For a density of the plasticized material, ρ=1000 kg/m³, a flow rate, Q=2.83 mm³/s, an effective viscosity, $\mu_{s,n}$=40 Pa·s (as shown in the non-limiting example 11 below), and the exit radius, $R_n=250$ μm, the Reynolds number, $Re=2\rho v R_n/\mu_{s,n}=2\rho Q/\pi\mu_{s,n}R_n=1.8\times 10^{-4}$, where v is the velocity of the plasticized material at the exit.

For the non-limiting values above and a non-limiting surface tension of the plasticized material, σ=0.04 N/m, the capillary number, $Ca=\mu_{s,n}v/\sigma\approx\mu_{s,n}Q/\pi R_n^2\sigma=14.4$.

Example 11: Shear Strain Rate in Wet Material During Flow Through Exit Port

During flow through an exit port of the extrusion channel, the shear strain rate in the wet, plasticized material may be estimated by the following rough approximation:

$$\dot{\gamma}_{s,n} \approx \frac{Q}{\pi R_n^3} \tag{28}$$

Thus for the non-limiting values, $Q=2.83$ mm$^3$/s and $R_n=250$ μm, $\dot{\gamma}_{s,n}\approx 58$ 1/s. The shear viscosity of the non-limiting wet material considered in the examples herein was about 40 Pa·s at this shear strain rate as shown in FIG. 25.

Example 12: Shear Strain Rate and Viscosity of Bending Fibers

In a bending fiber as shown schematically in FIG. 10a, the uniform load applied between the contacts, due to the self-weight of the bending fiber, may induces a normal stress in the bending fiber. For linear elastic deformation, the maximum normal stress at the midspan may be estimated by:

$$\sigma_{max} = \frac{MR_p}{I} \tag{29a}$$

Substituting the bending moment, $M=q\lambda_p^2/24$, the moment of inertia, $I=\pi R_p^4/4$, and the weight per unit length, $q=\pi R_p^2 \rho g$, gives:

$$\sigma_{max} = \frac{\rho g \lambda_p^2}{6R_p} \tag{29b}$$

If the stress is uniaxial, the maximum shear stress, $\tau_{max}$, may act on a plane at 45° to the neutral axis. By Mohr's circle construction, $$\tau_{max} = \frac{\sigma_{max}}{2} = \frac{\rho g \lambda_p^2}{12R_p} \tag{30}$$

Thus, for a linear elastic, incompressible material and small deflections, the shear strain may be estimated by:

$$\gamma_{max} = \frac{\tau_{max}}{G} = \frac{\rho g \lambda_p^2}{12GR_p} \tag{31}$$

where G is the shear modulus.

Analogous to the elastic solution, the shear strain rate at the outer edge of an incompressible, Newtonian viscous fiber may be approximated as:

$$\dot{\gamma}_{max} = \frac{\tau_{max}}{\mu_s} = \frac{\rho g \lambda_p^2}{12\mu_s R_p} \tag{32}$$

The material considered in the non-limiting experimental example 4, however, was non-Newtonian viscous, and thus Eq. (32) is not quite valid. Nonetheless, substituting the mean strain rate, $\dot{\bar{\gamma}}_p$ in the constitutive equation $\mu_s=m\dot{\bar{\gamma}}_p^{n-1}$ and inserting in Eq. (32) gives the following rough estimate of $\dot{\bar{\gamma}}_p$:

$$\dot{\bar{\gamma}}_p \approx \frac{\dot{\gamma}_{max}}{2} = \left(\frac{\rho g \lambda_p^2}{24mR_p}\right)^{1/n} \tag{33}$$

Using the non-limiting values ρ=1000 kg/m$^3$, $R_p$=250 μm, $\lambda_p$=900 μm, m=321 Pa·s$^n$, and n=0.35, $\dot{\bar{\gamma}}_p$=1.5×10$^{-7}$ 1/s. The shear viscosity was not measured at such small strain rates (FIG. 25). The shear viscosity at the lowest measured strain rate was 6220 Pa·s.

Example 13: Shear Strain Rate and Viscosity of Contacting Crossed Fibers

The maximum shear stress in elastic contact of crossed fibers may be roughly estimated by (see, e.g., K. L. Johnson, "Contact mechanics", Cambridge University Press, 1985):

$$\tau_{max} = 0.465\frac{P}{\pi a^2} = 0.465\frac{\rho g R_p^2 \lambda_p n_p}{a^2} \tag{34}$$

Thus, similar to the analysis above, the mean shear strain rate may be estimated as:

$$\dot{\bar{\gamma}}_p \approx \left(\frac{\tau_{max}}{2m}\right)^{1/n} = 0.233^{1/n}\left(\frac{\rho g R_p^2 \lambda_p n_p}{a^2 m}\right)^{1/n} \tag{35}$$

where a is the contact radius and $n_p$ the number of fibers above a deformable contact.

By way of example but not by way of limitation, if ρ=1000 kg/m$^3$, $R_p$=250 μm, $\lambda_p$=900 μm, $n_p$=2, a $R_p/2$=125 μm, the mean shear strain rate, $\dot{\bar{\gamma}}_p\approx 0.165$ 1/s and $\mu_{s,m}$=1035 Pa·s (FIG. 25).

Example 14: Estimation of the Time During which Crossed Fiber Contact is Deformable The shear stress in contacting fibers may be maximal at a distance roughly 0.5a underneath the contact (see, e.g., K. L. Johnson, "Contact mechanics", Cambridge University Press, 1985). Thus using a $R_p/2$, the shear stress may be maximal at the position r≈0.75$R_p$ in the fiber. From the graphical solution to Eq. (16) given by Crank, the solvent concentration at this position has decreased by about 50% after the time $t \approx 0.06 R_p^2/D_{solv}$. Thus, the time during which the crossed fiber contact is deformable, $$\tau_{def} \approx 0.06 \frac{R_p^2}{D_{solv}} \tag{36}$$

where $D_{solv}$ is the diffusivity of the solvent molecules in the fiber. Using the non-limiting values $D_{solv}=2.5\times10^{-10}$ m$^2$/s and $R_p=250$ µm, $\tau_{def}\approx 15$ seconds.

Additional Application Examples

The applicability of the method and apparatus herein is not limited to the processing of pharmaceutical materials (e.g., active ingredients and excipients) and the manufacture of fibrous dosage forms. The method and apparatus may also be applied for the manufacture of fibrous structures more generally. In the context of the invention herein, a fibrous structure is referred to a solid structure that is prepared from at least one fiber. Thus, a fibrous structure may comprise a solid having an outer surface and an internal structure contiguous with and terminating at said outer surface. The internal structure may comprise a three dimensional structural network of one or more fibers. The fibers may further comprise fiber segments separated and spaced from adjoining fiber segments by free spacings, $\lambda_f$, which define one or more free spaces in the solid. The solid is not limited to a drug-containing solid. It may comprise an organic material, such as a food or food-like material (e.g., starch (e.g., potato starch, rice starch, corn starch, pregelatinized starch, etc.), amylose, amylopectin, polysaccharides, chocolate liquor, cocoa butter, cocoa, cocoa paste, fat, carbohydrates, lipids, proteins, vitamins, sweeteners (e.g., sugars or polyols (e.g. glucose, sucrose, mannitol, maltitol, sorbitol, maltodextrin, xylitol, etc.), etc.), a polymer (e.g., polyethylene, polypropylene, polystyrene, polycarbonate. acrylonitrile butadiene styrene, etc.), a protein (e.g., collagen, glutelin, etc.), or an inorganic material, such as a metal (e.g., iron, aluminum, steel, stainless steel, copper, iridium, platinum, tungsten, etc.) or a ceramic.

CONCLUDING REMARKS

In conclusion, this invention discloses a method and an apparatus for the manufacture of solid dosage forms with tailor-made microstructure. The manufacturing process disclosed herein is predictable, highly economical, and enables short process times.

It is contemplated that a particular feature described either individually or as part of an embodiment in this disclosure can be combined with other individually described features, or parts of other embodiments, even if the other features and embodiments make no mention of the particular feature. Thus, the invention herein extends to such specific combinations not already described. Furthermore, the drawings and embodiments of the invention herein have been presented as examples, and not as limitations. Thus, it is to be understood that the invention herein is not limited to these precise embodiments. Other embodiments apparent to those of ordinary skill in the art are within the scope of what is claimed.

We claim:

1. A method of manufacturing pharmaceutical solid dosage forms comprising the steps of:
   injecting at least one active ingredient, at least one excipient, and at least one solvent into an extrusion channel having a cross section extending along its length inside a housing;
   mixing the at least one active ingredient, the at least one excipient, and the at least one solvent to form a plasticized matrix;
   conveying the plasticized matrix towards an exit port of the extrusion channel by applying mechanical work on the plasticized matrix;
   extruding the plasticized matrix through an exit port to form one or more plasticized fibers;
   structuring one or more plasticized fibers to a three dimensional structural network by depositing said fibers along a path defined by motion of a translating or rotating stage; and
   solidifying the deposited three dimensional structural network of one or more fibers by application of a gas flow through said network.

2. The method of claim 1, wherein at least one excipient is injected as a granular solid.

3. The method of claim 1, wherein the stage is movable in at least three directions relative to the exit port for depositing one or more plasticized fibers along a path defined by motion of said stage.

4. The method of claim 1, wherein two directions in which the stage is movable span a plane oriented at an angle to the central axis of the extruded fiber to pattern said fiber on a substrate defined by or attached to said stage, and wherein said stage is further movable in a third direction oriented at an angle to said plane to control the distance between said substrate and the exit port.

5. The method of claim 1, wherein gas flow is applied using a gas blowing unit.

6. The method of claim 1, wherein gas flow through the deposited fiber network promotes solidification by evaporating solvent or by cooling.

7. The method of claim 1, wherein the stage comprises at least a perforation through which gas flows for solidifying the deposited structure.

8. The method of claim 1, wherein the stage comprises a solid grid having at least a perforation through which gas flows for solidifying the deposited structure.

9. The method of claim 1, wherein at least one exit port is designed to extrude fiber having a fiber thickness less than 2.5 mm.

10. The method of claim 1, wherein the three dimensional structural network of one or more drug-containing fibers is solidified by evaporating solvent from at least one plasticized fiber or by cooling at least one plasticized fiber.

11. The method of claim 1, wherein the application of mechanical work on the plasticized matrix is performed using at least one screw.

12. The method of claim 1, wherein the weight fraction of solvent in a plasticized fiber is no greater than 0.925.

13. A method of manufacturing pharmaceutical solid dosage forms comprising the steps of:
   injecting one or more active ingredients and one or more excipients into an extrusion channel having a cross section extending along its length inside a housing, wherein the at least one excipient melts upon heating;
   heating the injected one or more active ingredients and one or more excipients to form a plasticized matrix;

conveying the plasticized matrix towards an exit port of the extrusion channel by applying mechanical work on the plasticized matrix;

extruding the plasticized matrix through an exit port to form one or more plasticized fibers;

structuring one or more plasticized fibers to a three dimensional structural network by depositing said fibers along a path defined by motion of a translating or rotating stage; and solidifying the deposited three dimensional structural network of one or more fibers by application of a gas flow through said network.

14. The method of claim 1, wherein the at least one excipient is injected as a granular solid.

15. The method of claim 1, wherein the stage is movable in at least three directions relative to the exit port for depositing the one or more plasticized fibers along a path defined by motion of said stage.

16. The method of claim 1, wherein two directions in which the stage is movable span a plane oriented at an angle to the central axis of the extruded fiber to pattern said fiber on a substrate defined by or attached to said stage, and wherein said stage is further movable in a third direction oriented at an angle to said plane to control the distance between said substrate and an exit port.

17. The method of claim 1, wherein gas flow is applied using a gas blowing unit.

18. The method of claim 1, wherein the gas flow through the deposited fiber network promotes solidification of the network by cooling.

19. The method of claim 1, wherein the stage comprises at least a perforation through which the gas flows for solidifying the deposited structure.

20. The method of claim 1, wherein the stage comprises a solid grid having at least a perforation through which the gas flows for solidifying the deposited structure.

21. The method of claim 1, wherein the at least one exit port is designed to extrude fiber having a fiber thickness less than 2.5 mm.

22. The method of claim 1, wherein the application of mechanical work on the plasticized matrix is performed using at least one screw.

23. A pharmaceutical solid dosage form comprising:

a drug-containing solid comprising a three dimensional fiber network structure;

said three dimensional fiber network structure comprising one or more fibers with average fiber thickness in the range of 1.75 µm to 2.5 mm;

said fibers having at least one active ingredient and at least one excipient through the fiber thickness;

said fibers further comprising fiber segments separated and spaced from adjoining fiber segments by free spacings; and the free spacings defining one or more free spaces in the drug-containing solid;

wherein the dosage form is manufactured by a method comprising the steps of:

injecting one or more active ingredients and one or more excipients into an extrusion channel having a cross section extending along its length inside a housing, wherein at least one excipient melts upon heating;

heating the injected one or more active ingredients and one or more excipients to form a plasticized matrix;

conveying the plasticized matrix towards an exit port of the extrusion channel by applying mechanical work on the plasticized matrix;

extruding the plasticized matrix through the exit port to form one or more plasticized fibers;

structuring one or more plasticized fibers to a three dimensional structural network by depositing said fibers along a path defined by motion of a translating or rotating stage; and solidifying the deposited three dimensional structural network of one or more fibers by application of a gas flow through said network.

24. A pharmaceutical solid dosage form comprising:

a drug-containing solid comprising a three dimensional fiber network structure;

said three dimensional fiber network structure comprising one or more fibers with average fiber thickness in the range of 1.75 µm to 2.5 mm;

said fibers having at least one active ingredient and at least one excipient through the fiber thickness;

said fibers further comprising fiber segments separated and spaced from adjoining fiber segments by free spacings; and the free spacings defining one or more free spaces in the drug-containing solid;

wherein the dosage form is manufactured by a method comprising the steps of:

injecting at least one active ingredient, at least one excipient, and at least one solvent into an extrusion channel having a cross section extending along its length inside a housing;

mixing the at least one active ingredient, the at least one excipient, and the at least one solvent to form a plasticized matrix;

conveying the plasticized matrix towards an exit port of the extrusion channel by applying mechanical work on the plasticized matrix;

extruding the plasticized matrix through the exit port to form one or more plasticized fibers;

structuring one or more plasticized fibers to a three dimensional structural network by depositing said fibers along a path defined by motion of a translating or rotating stage; and solidifying the deposited three dimensional structural network of one or more fibers by application of a gas flow through said network.

* * * * *